(12) United States Patent
Werner et al.

(10) Patent No.: US 8,053,632 B2
(45) Date of Patent: Nov. 8, 2011

(54) METHOD OF CONTROLLING CELLULAR PROCESSES IN PLANTS

(75) Inventors: Stefan Werner, Halle/Saale (DE); Sylvestre Marillonnet, Halle/Saale (DE); Victor Klimyuk, Halle/Saale (DE); Yuri Gleba, Halle/Saale (DE)

(73) Assignee: Icon Genetics GmbH, München (DE)

( * ) Notice: Subject to any disclaimer, the term of this patent is extended or adjusted under 35 U.S.C. 154(b) by 265 days.

(21) Appl. No.: 10/535,780

(22) PCT Filed: Nov. 20, 2003

(86) PCT No.: PCT/EP03/13018
§ 371 (c)(1),
(2), (4) Date: Jun. 22, 2005

(87) PCT Pub. No.: WO2004/046360
PCT Pub. Date: Jun. 3, 2004

(65) Prior Publication Data
US 2006/0026718 A1    Feb. 2, 2006

(30) Foreign Application Priority Data
Nov. 20, 2002  (DE) ................................ 102 54 166

(51) Int. Cl.
*C12N 15/82* (2006.01)
*C12N 15/00* (2006.01)
*C12N 15/09* (2006.01)
*C12N 15/33* (2006.01)

(52) U.S. Cl. ........ 800/280; 800/278; 800/279; 800/288; 435/320.1; 435/440; 435/468; 536/23.1; 536/23.72

(58) Field of Classification Search .................. None
See application file for complete search history.

(56) References Cited

U.S. PATENT DOCUMENTS

| 2002/0046419 A1 | 4/2002 | Choo et al. |
| 2002/0143142 A1 | 10/2002 | Lin et al. |

FOREIGN PATENT DOCUMENTS

| JP | 2000-500323 | | 1/2000 |
| WO | WO 95/21248 A1 | | 8/1995 |
| WO | WO 98/37211 | | 8/1998 |
| WO | WO 99/52563 A1 | | 10/1999 |
| WO | WO0071701 | * | 5/2000 |
| WO | WO0071701 | * | 11/2000 |
| WO | WO 01/38488 A2 | | 5/2001 |
| WO | WO0189283 | * | 5/2001 |
| WO | WO 01/89283 A1 | | 11/2001 |
| WO | WO 02/088369 A1 | | 11/2002 |
| WO | WO0189283 | * | 11/2002 |

OTHER PUBLICATIONS

Mackenzie 2005 Trends in Cell Biology 15:548-554.*
Jo, E., et al., "Epigenetic Regulation of Gene Structure and Function with a Cell-Permeable Cre Recombinase," *Nature Biotechnology*, 2001, pp. 929-933, vol. 19, Nature Publishing Group.
O'Donnell, P., et al., "A Novel Tomato Gene that Rapidly Responds to Wound- and Pathogen-Related Signals," *The Plant Journal*, 1998, pp. 137-142, vol. 14(1), Blackwell Science Ltd.
Pearce, G., et al., "A Polypeptide from Tomato Leaves Induces Wound-Inducible Proteinase Inhibitor Proteins," *Science Reports*, 1991, pp. 895-898, vol. 23.
Will, E., et al., "Unmodified Cre Recombinase Crosses the Membrane," *Nucleic Acids Research*, 2002, pp. 1-6, vol. 30(12)e59, Oxford University Press.
Zhang, Y., et al., "Efficient and Inducible Production of Human Interleukin 6 in Chinese Hamster Ovary Cells Using a Novel Expression System," *Cytotechnology*, 1997, pp. 53-60, vol. 25, Kluwer Academic Publishers, Netherlands.
Cao, Ming-Xia et al., "Site-Specific DNA Excision in Transgenic Rice With a Cell-Permeable Cre Recombinase," *Molecular Biotechnology*, 2006, vol. 32, pp. 55-63.
Thyagarajan, B., et al., "Mammalian genomes contain active recombinase sites," *Gene*, 2000, vol. 244, pp. 47-54.
Schmidt, E., et al., "Illegitimate Cre-dependent chromosome rearrangements in transgenic mouse spermatids," *PNAS*, 2000, vol. 97(25), pp. 13702-13707.
"Chemistry of Organisms—Chemistry in Treating Diseases from Gene Therapy to Protein Therapy," *Chemistry*, 2002, vol. 57(9), pp. 50-55.

* cited by examiner

*Primary Examiner* — Brent T Page
(74) *Attorney, Agent, or Firm* — Alston & Bird LLP

(57) ABSTRACT

A method of controlling a genetically-modified plant, comprising (a) providing a genetically-modified plant, whereby cells of said genetically-modified plant contain a heterologous nucleic acid and whereby said genetically-modified plant is inactive with regard to a cellular process of interest, (b) switching on said cellular process of interest by directly introducing a polypeptide from a cell-free composition into cells containing said heterologous nucleic acid wherein said polypeptide and said heterologous nucleic acid are mutually adapted such that said polypeptide is capable of switching on said cellular process of interest.

19 Claims, 9 Drawing Sheets

METHOD OF CONTROLLING CELLULAR PROCESSES IN PLANTS

CROSS-REFERENCE TO RELATED APPLICATIONS

This application is the U.S. National Stage of International Application PCT/EP2003/013018 filed Nov. 20, 2003, which designates the U.S. and was published by the International Bureau in English on Jun. 3, 2004, and which claims the benefit of German Patent Application No. 102 54 166.3 filed Nov. 20, 2002; both of which are hereby incorporated herein in their entirety by reference.

FIELD OF THE INVENTION

The present invention relates to a method of controlling a cellular process of interest in a plant by an external signal like an externally applied polypeptide. The invention further relates to a transiently or stably genetically-modified plant adapted for said method and to a genetically-modified plant which has been controlled according to the method of the invention. Moreover, the present invention relates to a method of producing a product in a genetically-modified plant by controlling a cellular process of interest using an encrypted external signal. The process of the invention allows for the selective control of transgene expression in a transiently or stably genetically modified plant, whereby a cellular process of interest previously non-operable in the plant may be selectively switched on at any predetermined time.

BACKGROUND OF THE INVENTION

Controllable Transagene Expression Systems in Plants

One of the major problems in plant biotechnology is the achievement of reliable control over transgene expression. Tight control over gene expression in plants is essential if a downstream product of transgene expression is growth inhibitory or toxic, like for example, biodegradable plastics (Nawrath, Poirier & Somerville, 1994, *Proc. Natl. Acad. Sci.*, 91, 12760-12764; John & Keller, 1996, *Proc. Natl. Acad. Sci.*, 93, 12768-12773; U.S. Pat. Nos. 6,103,956; 5,650,555) or protein toxins (U.S. Pat. No. 6,140,075). Existing technologies for controlling gene expression in plants, are usually based on tissue-specific and inducible promoters and practically all of them suffer from a basal expression activity even when uninduced, i.e. they are "leaky". Tissue-specific promoters (U.S. Pat. No. 5,955,361; WO09828431) represent a powerful tool but their use is restricted to very specific areas of applications, e.g. for producing sterile plants (WO9839462) or expressing genes of interest in seeds (WO00068388; U.S. Pat. No. 5,608,152). Inducible promoters can be divided into two categories according to their induction conditions: those induced by abiotic factors (temperature, light, chemical substances) and those that can be induced by biotic factors, for example, pathogen or pest attack. Examples of the first category are heat-inducible (U.S. Pat. No. 5,187,287) and cold-inducible (U.S. Pat. No. 5,847,102) promoters, a copper-inducible system (Mett et al., 1993, *Proc. Natl. Acad. Sci.*, 90, 4567-4571), steroid-inducible systems (Aoyama & Chua, 1997, *Plant J.*, 11, 605-612; McNellis et al., 1998, *Plant J.*, 14, 247-257; U.S. Pat. No. 6,063, 985), an ethanol-inducible system (Caddick et al., 1997, *Nature Biotech.*, 16, 177-180; WO09321334), and a tetracycline-inducible system (Weinmann et al., 1994, *Plant J.*, 5, 559-569). One of the latest developments in the area of chemically inducible systems for plants is a chimaeric promoter that can be switched on by glucocorticoid dexamethasone and switched off by tetracycline (Bohner et al., 1999, *Plant J.*, 19, 87-95). For a review on chemically inducible systems see: Zuo & Chua, (2000, *Current Opin. Biotechnol.*, 11, 146-151). Other examples of inducible promoters are promoters which control the expression of patogenesis-related (PR) genes in plants. These promoters can be induced by treatment of a plant with salicylic acid, an important component of plant signaling pathways in response to pathogen attack, or other chemical compounds (benzo-1,2,3-thiadiazole or isonicotinic acid) which are capable of triggering PR gene expression (U.S. Pat. No. 5,942,662).

There are reports of controllable transgene expression systems using viral RNA/RNA polymerase provided by viral infection (for example, see U.S. Pat. Nos. 6,093,554; 5,919, 705). In these systems, a recombinant plant DNA sequence includes the nucleotide sequences from the viral genome recognized by viral RNA/RNA polymerase. The effectiveness of these systems is limited because of the low ability of viral polymerases to provide functions in trans, and their inability to control processes other than RNA amplification. Another way is to trigger a process of interest in a transgenic plant by using a genetically-modified virus which provides a heterologous nucleic acid encoding a switch for a biochemical process in a genetically-modified plant (WO02068664).

The systems described above are of significant interest as opportunities of obtaining desired patterns of transgene expression, but they do not allow tight control over the expression patterns, as the inducing agents (copper) or their analogs (brassinosteroids in case of steroid-controllable system) can be present in plant tissues at levels sufficient to cause residual expression. Additionally, the use of antibiotics and steroids as chemical inducers is not desirable or economically unfeasible for large-scale applications. When using promoters of PR genes or viral RNA/RNA polymerases as control means for transgenes, the requirements of tight control over transgene expression are also not fulfilled, as casual pathogen infection or stress can cause expression. Tissue- or organ-specific promoters are restricted to very narrow areas of application, since they confine expression to a specific organ or stage of plant development, but do not allow the transgene to be switched on at will. Recombinant viral switches as described in WO02/068664 address all these problems, but do not guarantee tight environmental safety requirements, as the heterologous nucleic acid in the viral vector can recombine.

There is an abundant literature including patent applications which describe the design of virus resistant plants by the expression of viral genes or mutated forms of viral RNA (e.g. U.S. Pat. Nos. 5,792,926; 6,040,496). However, there is an environmental risk associated with the use of such plants due to the possibility of forming novel viruses by recombination between the challenging virus and transgenic viral RNA or DNA (Adair & Kearney, 2000, *Arch. Virol*, 145, 1867-1883).

Hooykaas and colleagues (2000, *Science*, 290, 979-982; WO01/89283) described the use of a translational fusion of Cre recombinase with vir gene fragments for *Agrobacterium*-mediated recombinase translocation into plant cells. Cre-mediated in planta recombination events resulted in a selectable phenotype. The translocation of Cre recombinase is the first use of a translocated protein as a switch to trigger a process of interest in plant cells. However, despite the translocation is not necessarily accompanied by DNA transfer, this approach does not guarantee high level safety, as the phytopathogenic genetically-modified microorganism (*Agrobacterium*) posesses a complete coding sequence of the switching protein Cre recombinase. Further, the process of interest can only be triggered in cells that receive the switching protein. If large ensembles of cell are to be treated, the ratio of cells receiving switching protein to the total number of cells becomes very small. The method of Hooykaas can therefore not be applied to entire plants. Instead, its usefulness is limited to cells in tissue culture or cell culture.

It is therefore object of this invention to provide a method of switching on a cellular process of interest in entire plants. It is another object of the invention to provide an environmentally safe method of switching on a cellular process of interest in plants, whereby the cellular process may be selectively switched on at any predetermined time. It is another object of this invention to provide a method for producing a product in a transgenic plant, wherein the production of the product may be selectively switched on after the plant has grown to a desired stage, whereby the process is environmentally safe in that genetic material necessary for said cellular process and genetic material coding for the control function are not spread in the environment together.

GENERAL DESCRIPTION OF THE INVENTION

The above objects are achieved by a method of controlling a genetically-modified plant, comprising
(a) providing a genetically-modified plant, whereby cells of said genetically-modified plant contain a heterologous nucleic acid and whereby said genetically-modified plant is inactive with regard to a cellular process of interest,
(b) switching on said cellular process of interest by directly introducing a polypeptide from a cell-free composition into cells containing said heterologous nucleic acid,
wherein said polypeptide and said heterologous nucleic acid are mutually adapted such that said polypeptide is capable of switching on said cellular process of interest.

The invention also provides genetically-modified plants or parts thereof obtained or obtainable by the method of the invention. Preferred parts of said plants are leaves and seeds. Seeds are most preferred examples for parts of a plant.

The invention also provides a genetically-modified plant containing a heterologous nucleic acid in cells thereof, wherein said plant is inactive with regard to a cellular process of interest, wherein said heterologous nucleic acid is adapted such that said cellular process of interest can be switched on by directly introducing a polypeptide into cells containing said heterologous nucleic acid, wherein said polypeptide and said heterologous nucleic acid are mutually adapted such that said polypeptide is capable of switching on said cellular process of interest.

Further, the invention provides a system for controlling a cellular process of interest in a genetically-modified plant, comprising a plant as defined above and a polypeptide for switching on said cellular process of interest in the genetically-modified plant, whereby said plant and said polypeptide are mutually adapted such that said polypeptide is capable of switching on said cellular process of interest.

The present invention allows to switch on a cellular process of interest in a plant by directly introducing a polypeptide into cells that contain said heterologous nucleic acid. Directly introducing said polypeptide means that said introducing does not comprise applying nucleic acids to said plant that code for said polypeptide or for a functional part of said polypeptide. A part of said polypeptide is functional if it is capable of switching on the cellular process of the invention. By said direct application of said polypeptide to said plant, a very high level of biological safety is achieved by the invention, since the plant does not come into contact with genetic material that could switch on said cellular process of interest. Instead, at least one necessary component for said cellular process is provided to the plant as a polypeptide without genetic material coding for said polypeptide. A major advantage of the invention is that genetic material necessary for the cellular process of interest and genetic material coding for said polypeptide cannot both be transferred to progeny of said plant or otherwise spread together in the environment.

The method of Hooykaas (2000, *Science*, 290, 979-982; WO01/89283) allows switching on a cellular process of interest in plant cells, whereby a switching protein is introduced using pathogenic bacteria. As this method is limited to cell culture (laboratory scale), biological safety concerns due to the use of *Agrobacteria* that code for the switching protein do not arise. The present invention provides for the first time a method of controlling a cellular process of interest that is efficient in whole plants and that is at the same time environmentally safe even when used on a large scale like in a green-house or on a farm field.

In step (a) of the method of the invention, a genetically-modified plant is provided. Higher plants, notably higher crop plants, are preferred. Said plant is genetically-modified in that cells of said plant contain a heterologous nucleic acid that is involved in switching on said cellular process of interest. In many cases, said heterologous nucleic acid may code for a protein to be expressed. Said plant provided in step (a) may be a transgenic plant, whereby most or all of the cells of said plant contain said heterologous nucleic acid stably integrated in the genome of said cells. Said heterologous nucleic acid may be stably integrated into the nuclear genome or in the genome of organelles like mitochondria or, preferably, plastids. Integration of said heterologous nucleic acid in the plastid genome is advantageous in terms of biological safety. The method of the invention is preferably carried out with transgenic plants. Alternatively, however, said plant may be transiently modified and/or said heterologous nucleic acid may be present in a fraction of cells but not in other cells. A heterologous nucleic acid in a transiently modified plant may be stably integrated in the genome of said fraction of cells or it may be present episomally. Incorporation of said heterologous nucleic acid in a fraction of cells of said plant may be achieved by transiently transfecting said organism e.g. using viral transfection or *Agrobacterium*-mediated transformation. In any case, the genetically-modified plant provided in step (a) is inactive with regard to the cellular process of interest before step (b) has been carried out.

In step (b) of the method of the invention, said polypeptide is introduced from a cell-free composition into at least some of said cells containing said heterologous nucleic acid. If said plant is transgenic, said polypeptide may in principal be applied to any part or to any cells of the plant. If only a fraction of the cells of said plant contains said heterologous nucleic acid, said polypeptide is applied to the plant such that said polypeptide can reach cells containing said heterologous nucleic acid for switching on the cellular process of interest. As noted above, said polypeptide is directly introduced into cells of said plant from a cell-free composition. A cell-free composition does not contain viable cells that could replicate nucleic acids coding for said polypeptide. Preferably, said cell-free composition contains no viable cells. A cell-free composition may be a cell extract obtained by lysing cells (e.g. cells like bacterial cells used for expressing said polypeptide), provided there are no viable cells in said composition that could replicate nucleic acids coding for said polypeptide. Other examples of cell-free compositions are solutions, preferably buffered aqueous solutions, of said polypeptide or said polypeptide in solid or dry form, provided there are no viable cells as defined above.

Directly introducing may be done by (i) particle (microprojectile) bombardment, (ii) application of said polypeptide on at least a part of said plant, or (iii) by injecting a solution containing said polypeptide in tissue of said plant. In methods (ii) and (iii), said polypeptide is typically contained in a liquid, preferably aqueous, cell-free composition (or solution) that is applied to parts of the plant. Such a composition may be applied e.g. by spraying said plant with said composition containing the polypeptide. Further, said composition may be injected according to (iii).

For methods (ii) and (iii), said polypeptide preferably comprises a membrane translocation sequence (MTS) that enables entering of said polypeptide into cells of said plant. Said membrane translocation sequence may be covalently or non-covalently bound to said polypeptide. Preferably, it is covalently bound to said polypeptide. Said membrane translocation sequence may be a peptide that endows said polypeptide with the capability of crossing the plasma membrane of cells of said organism. Many such membrane translocation sequences are known in the art. Frequently, they comprise several basic amino acids, notably arginines. The size of membrane translocation sequences may vary largely, however, they may typically have 3 to 100 amino acids, preferably 5 to 60 amino acids. Said polypeptide may be produced by standard protein expression techniques e.g. in *E. coli*. Purification of said polypeptide after its expression is preferably done, notably removal or destruction of nucleic acids coding for said polypeptide. Nucleic acids may be removed or destroyed by hydrolysis, preferably catalysed by an enzyme like a (DNase) or a ribonuclease (RNase). Further or additionally, chromatographic techniques may be used for removing nucleic acids from said polypeptide. Said polypeptide may be applied to a plant e.g. by spraying said plant with a liquid composition, preferably an aqueous solution, containing said polypeptide. Preferably, measures are taken to facilitate entering of said polypeptide into cells of a plant, notably measures that allow crossing of the plant cell wall and/or the outer plant layer. An example of such measures is slight wounding of parts of the plant surface e.g. by mechanical scratching. Another example is the use of cellulose-degrading enzymes to weaken or perforate the plant cell wall.

Switching on of the cellular process of interest (step (b)) requires directly introducing said polypeptide from a cell-free composition into cells that contain said heterologous nucleic acid. Said polypeptide and said heterologous nucleic acid are mutually adapted such that said polypeptide is capable of switching on said cellular process of interest.

With respect to said cellular process of interest, there are no particular limitations and the invention is of very broad applicability. Said cellular process of interest may be or may comprise formation of a DNA, an RNA or a protein from said heterologous nucleic acid or involving said heterologous nucleic acid. There are numerous possibilities for achieving formation of said DNA, said RNA or said protein. Said polypeptide may for example comprise a segment having a binding activity to said heterologous nucleic acid, e.g. to a promoter. Said segment may then e.g. act as a transcription factor inducing transcription of said hetereologous nucleic acid, thus triggering formation of said RNA and or said protein.

Preferably, said polypeptide has a segment having an enzymatic activity capable of triggering formation of said DNA, said RNA or said protein. Examples of such activities are DNA or RNA-modifying activities like the activity of a site-specific recombinase, flippase, resolvase, integrase, polymerase, or a transposase. Said enzymatic activity may modify said heterologous nucleic acid leading to expression of said protein e.g. by recombination. In an embodiment wherein said polypeptide has polymerase activity, said segment may be a DNA-dependent RNA polymerase that acts on a promoter of said heterologous nucleic acid. Said promoter is preferably not recognized by native polymerases of said plant. Examples of such promoter-polymerase systems are bacterial, viral, or bacteriophage promoter-polymerase systems like the T7 promoter-T7 polymerase.

Moreover, said switching on of said cellular process of interest may comprise formation of a DNA, an RNA or a protein from said heterologous nucleic acid or involving said heterologous nucleic acid. As an example, the formation of an expressible operon from said heterologous nucleic acid or from an RNA expression product of said heterologous nucleic acid may be mentioned.

A sequence portion of said heterologous nucleic acid (or of said additional nucleic acid described below) may be operably linkable to a transcription promoter by the action of said protein, which allows to switch on expression of a protein of interest or transcription of an RNA-viral amplicon from said additional heterologous nucleic acid, e.g. by operably linking a sequence encoding said protein of interest or an RNA amplicon with a promoter. There are several ways of reducing this embodiment to practice. One option is to separate, in said (additional) heterologous nucleic acid, the sequence encoding an RNA amplicon and a promoter by a sequence block that precludes an operable linkage therebetween. Said sequence block may be flanked by recombination sites such that said block can be cut out by a recombinase recognizing said recombination sites. Thereby, operable linkage for transcription of the sequence encoding an RNA amplicon can be established and expression may be switched on. Another option is to have a portion of a sequence necessary for transcription (e.g. a promoter or promoter portion) in flipped orientation and flanked by recombination sites. Providing a suitable recombinase (e.g. with said polypeptide) may flip said sequence portion back in correct orientation, whereby an operable linkage can be established.

Further, said DNA, said RNA or said protein may be capable of spreading to other cells of said plant (e.g. a DNA or RNA viral vector). An important example of such a cellular process is the formation of an expressible amplicon from said heterologous nucleic acid or from an RNA expression product of said heterologous nucleic. Said amplicon is capable of amplifying within cells of its activation or formation (amplifying vector). Said amplicon may be an expressible amplicon that contains a gene of interest to be expressed in said cellular process of interest. Further, said amplicon may be capable of cell-to-cell or systemic movement in the plant of the invention. An amplicon may be based on a plant DNA or RNA virus. Plant RNA viruses like tobamoviruses are preferred. The amplification properties of said protein capable of spreading (see below) and said amplicon may behave synergistically, thus allowing an extremely strong cellular process of interest that spreads over significant parts of said plant (e.g. leading to extremely strong expression of a protein of interest from said amplicon). Engineering of amplicons based on Tobamoviruses is known in the art (see e.g. Dawson et al., 1989, *Virology*, 172, 285-293; Yusibov et al., 1999, *Curr. Top. Microbiol. Immunol.*, 240, 81-94; for review, see "Genetic Engineering With Plant Viruses", 1992, eds. Wilson and Davies, CRC Press, Inc.).

In a major embodiment of the invention, said switching on of said cellular process of interest involves formation of a protein from said heterologous nucleic acid, whereby said protein is capable of spreading within the plant, i.e. capable of leaving a cell of its formation and entering other cells of said plant (such a protein is also referred to as "protein switch" herein). In other cells, said protein may switch on a cellular process of interest, notably by controlling an additional heterologous nucleic acid (see below). Said leaving a cell and entering other cells preferably comprises cell-to-cell-movement or systemic movement in said plant or in a part thereof. Said protein (also referred to herein as "protein switch") preferably contains a protein portion enabling said leaving a cell and entering other cells of said protein switch. Said protein portion may be a domain of a viral movement protein or of a viral coat protein. Further, said protein portion may be a plant or an animal transcription factor, or a domain of a plant or animal transcription factor capable of cell-to-cell or systemic movement. Further, said protein portion may be a plant or animal peptide intercellular messenger, or a domain of a plant or an animal peptide intercellular messenger. Moreover, said protein portion may be an artificial peptide capable of enabling cell-to-cell or systemic movement. Preferably, however, said protein portion is or comprises a viral movement protein or viral coat protein, or a domain of a viral movement or coat protein.

When said protein capable of spreading enters other cells that contain said heterologous nucleic acid, it is preferably capable of switching on (inducing) expression of said protein from said heterologous nucleic acid. By making use of this protein (protein switch), the method of the invention allows to amplify and propagate the switching signal provided externally with said polypeptide in said plant. Particularly, if the number of cells initially reached by said polypeptide is small, the switching signal is efficiently carried to further cells in said plant. There are many ways how said protein can be made to control its own expression from said heterologous nucleic acid. These ways correspond to those that may be employed for said polypeptide of step (b) given above.

Apart from the capability of controlling its own expression, the protein has preferably the capability of switching on a cellular process of interest. Although switching on of a cellular process is preferred, it is clear to those skilled in the art that the end result of a cellular process that was switched on may also be a suppression or a switching off of a process in cells of the plant. For being capable of switching on said cellular process of interest, said protein may have a segment that is capable of controlling said cellular process. Said segment may have a binding activity or an enzymatic activity that controls a nucleic acid (notably said additional heterologous nucleic acid) necessary for said cellular process of interest. In the method of the invention, said switching on of said cellular process may be achieved analogously to the control of its own expression from said heterologous nucleic acid. For this purpose, said protein may have a segment for controlling said cellular process and a segment for causing said expression of said protein, whereby the control mechanisms of said two segments may be different. Preferably, the two control mechanisms are similar or identical, wherein one segment of said protein may be sufficient for switching on said cellular process and for controlling the expression of said protein. Thus, for simplicity, said protein contains most preferably said one segment and a portion endowing said protein with the capability of leaving a cell and entering other cells of said plant.

In the invention, said polypeptide of the invention can have the same switching function as said protein switch, e.g. have the same enzymatic activities as said protein switch. Said polypeptide is applied externally and can switch on a cellular process of interest in cells it enters. Said protein switch is produced inside cells of said genetically-modified plant, preferably in response to the switching function of said polypeptide. Said protein switch can in turn, after its production in cells of said plant, switch on a cellular process of interest in cells where it is produced and/or in other cells of said plant. If said polypeptide and said protein switch exert their switching function by the same of a related enzymatic activity, they may differ in that said polypeptide preferably has a membrane translocation sequence, whereas said protein switch preferably has a protein portion endowing said protein switch with the capability of leaving a cell and entering other cells.

Said cellular process of interest may require, as mentioned above, the presence of an additional heterologous nucleic acid in cells of said plant where said cellular process is to be controlled. Said additional heterologous nucleic acid may be present in all cells or in a fraction of cells of said plant. It may be stably incorporated in nuclear or organellar genomes of cells of said organism. What has been said regarding said heterologous nucleic acid of the invention generally applies also to said additional heterologous nucleic acid. Preferably, said plant is transgenic regarding said additional heterologous nucleic acid and regarding said heterologous nucleic acid.

Said additional heterologous nucleic acid will e.g. be made use of, if said heterologous nucleic acid is used for forming a protein capable of spreading in the plant. The spreading protein may then switch on a cellular process of interest encoded in said additional heterologous nucleic. FIG. 8 illustrates such an embodiment. The cellular process of interest that may be switched on from said additional heterologous nucleic corresponds to those mentioned in connection with said heterologous nucleic acid.

In a further important embodiment of this invention, a protein expressed from said heterologous nucleic acid and said directly introduced polypeptide jointly generate a predetermined function leading to switching on said cellular process of interest only when said protein and said polypeptide are jointly present (cf. FIG. 3). Preferably, said protein and said polypeptide jointly generate said predetermined function by intein-mediated trans-splicing or by intein-mediated affinity interaction. Said predetermined function may then switch on the cellular process of the invention. Said predetermined function may e.g. be a binding activity or an enzymatic activity that may act on said addtonal heterologous nucleic acid similar as described above for said protein. An important advantage of this embodiment is that the plant provided in step (a) that is genetically-modified with a heterologous nucleic acid does not contain all components required for switching on said cellular process of the invention. Thus, said plant cannot transfer genetic information for a functional cellular process or interest to progeny or to other organisms.

The cellular process of interest that was switched on as described herein does, however, not have to affect the entire plant. Instead, said cellular process of interest may be limited to a part of said plant like leaves or seeds. A cellular process of interest in seeds may be the production of a protein of interest in seeds, whereby the protein of interest can be easily harvested by conventional methods and stored in said seeds. Preferably, however, the cellular process of interest affects substantial parts of said plant. The part of a plant where said cellular process is switched on depends inter alia on the place(s) of application of said polypeptide. Generally, said cellular process of interest may be strongest in the vicinity of the place of application of said polypeptide and may decrease with increasing distance from said place. Said decrease may in general be anisotropic and depend on the structure of the tissue of said plant where said polypeptide was applied. If, for example, a cellular process of interest is to be switched on (e.g. expression of a gene of interest is to be switched on) and said polypeptide is applied to a fraction of a leaf of the plant, said cellular process of interest typically occurs within said fraction of said leaf and in the vicinity of said fraction of said leaf. Preferably, said cellular process of interest occurs in the major part of said leaf. More preferably, said cellular process of interest occurs also in the shoot and in other leaves. Most preferably, said cellular process of interest occurs in the major part of said plant. The extent of said cellular process of interest (e.g. expression of a gene of interest) may vary within said plant e.g. with the cell type or tissue type. Obviously, application of said polypeptide is normally not limited to a single point on the surface of a plant. Preferably, said polypeptide is applied to several parts of said plant (see further below).

The cellular process according to the invention may comprise or give rise to a whole biochemical cascade of interest like a multi-step biosynthetic pathway in cells of the plant. The cellular process or biochemical cascade of interest is not operable in the plant prior to exposure to said polypeptide. The method of the invention may provide control over a cellular process or biochemical cascade of interest with a hitherto unattainable technical precision and environmental safety. Thereby, novel applications in biotechnology in general, specifically in plant biotechnology, are available for solving problems which cannot be solved by conventional technologies like basal transgene expression activity in a plant, particularly when producing toxic substances or biodegradable polymers. Moreover, the precise control according to the invention allows to grow a transgenic plant to a desired stage where, for example, the plant is best suited for performing the cellular process of interest without burdening the plant with a basal expression activity slowing down the growth of the plant. Once the plant is ready for efficiently performing the cellular process of interest, the process of interest may be switched on and performed with high efficiency. Accordingly, the method of the invention allows to safely decouple the growth phase and the production phase of a multicellular organism, specifically a transgenic plant. Moreover, it is possible to design multi-component systems for multiple cellular processes or biochemical cascades of interest, whereby one or more desired processes or cascades can be selectively switched on.

FIG. 6 is a general scheme showing switching on a cellular process of interest via a protein-switch that is capable of intercellular trafficking and causing its own expression in other cells. PS stands for protein switch, TP stands for a trafficking protein capable of intercellular trafficking (i.e. leaving a cell and entering other cells), PS:TP stands for a PS-TP fusion protein, hNA stands for an additional heterologous nucleic acid.

(A) depicts a heterologous nucleic acid encoding PS:TP and an additional heterologous nucleic acid hNA. No external polypeptide is introduced, thus the protein switch is not expressed and no cellular process of interest is switched on.

(B) an external (cell-permeable) polypeptide is introduced causing expression of the protein-switch PS:TP. The protein switch can control a cellular process by acting on hNA in the cell of its expression. Further, the protein switch can leave the cell that was triggered by said externally introduced polypeptide and enter other cells. In other cells, the protein switch can induce its own expression and also control the cellular process by acting on hNA.

(C) depicts a heterologous nucleic acid encoding two protein switches: PS1 and PS2. Expression of PS1 is caused by an externally applied signal (the polypeptide of the invention), leading to PS1:TP. As above, PS1:TP can spread to other cells and activate expression of PS2. PS2 in turn can control a cellular process by acting on hNA.

FIG. 7 depicts in (A) the construct pICHGFPinv containing a non-functional TMV-based provector and in (B) a functional derivative of said construct resulting from integrase-mediated recombination. Arrows at the bottom indicate RNAs and subgenomic (sg) RNAs including their orientation that can be formed from the construct shown in (B). sgp stands for subgenomic promoter.

FIG. 8 shows schematically a method according to the invention, wherein a cell-permeable polypeptide (MTS:recombinase) triggers recombination events within targeted cells, leading to the formation of a protein switch capable of intercellular trafficking (recombinase:TP) from a heterologous nucleic acid (the construct coding for recombinase:TP). The protein switch can further trigger recombination events leading to rearrangement of a plant virus-based pro-vector (an additional heterologous nucleic acid according to the invention) resulting in expression of a gene of interest (GOI). MTS: membrane translocating sequence; TP: protein capable of intercellular trafficking; SM: selectable marker; RS: recombination site recognized by site-specific DNA recombinase/integrase; ter1 and ter2: transcription termination regions; PROM: promoter active in plants; RdRp: viral RNA-dependent RNA polymerase; MP: movement protein; 3'NTR: 3' non-translated region of plant RNA virus. Arrows show the orientation of coding and regulatory sequences.

Figure 9:
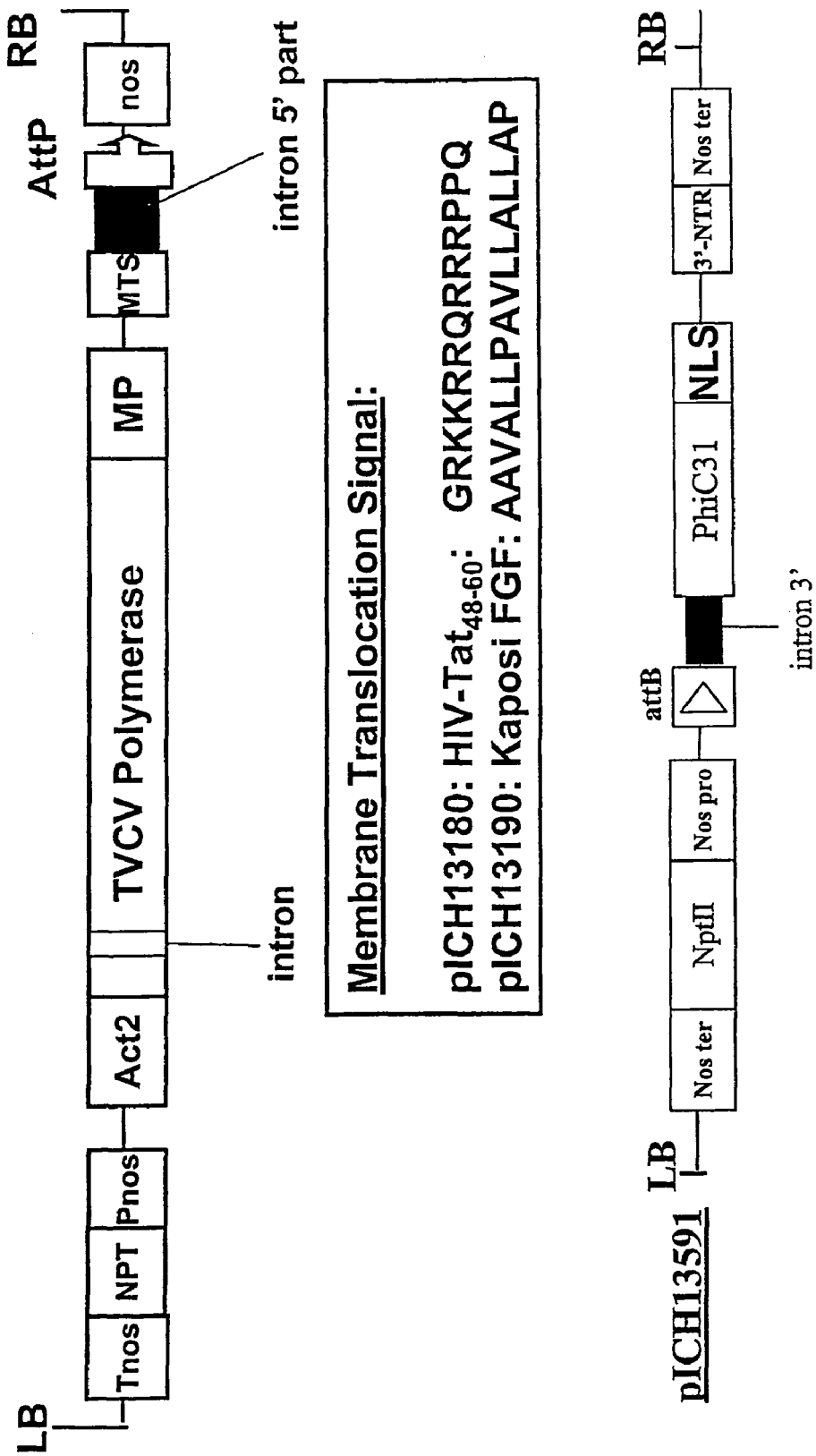

FIG. 9 shows vectors for producing integrase phiC31 proteins fused to membrane translocating signals (MTS). The vectors pICH13180 and pICH13190 contain the 5' end of a TMV-based vector with an MTS of choice and are designed for site-specific recombinase-mediated assembly with a vector (pICH13591) containing a 3' end of a TMV-based vector coding for the integrase phiC31 with nuclear localisation signal (NLS) at its C-terminal end. The membrane transloaction signals are: HIV-Tat$_{48-60}$ (SEQ ID NO:8) and Kaposi FGF (SEQ ID NO:6).

DETAILED DESCRIPTION OF THE INVENTION

At the basis of this invention is the use of a polypeptide capable of entering cells of a plant, leading to switching on a cellular process of interest without delivery of nucleic acids encoding said polypeptide or a functional part of said polypeptide into said cells. Preferably, said switching on a cellular process of interest comprises forming a protein that is capable of causing its own expression. The general principle of the method according to the invention is schematically shown in FIGS. 1 to 9.

Choice of Protein for "Switch" Function

Figure 1:
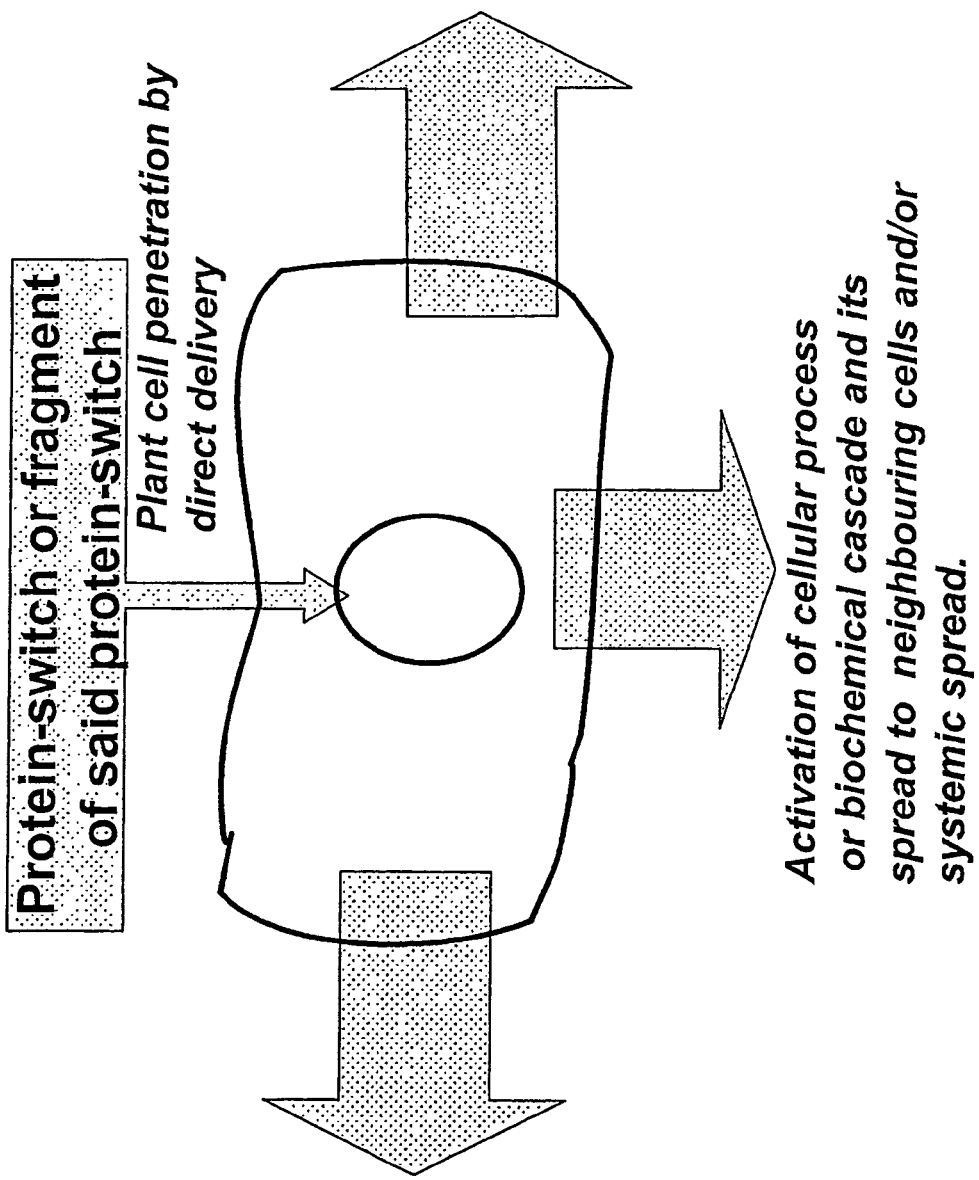
FIG. 1 is a scheme of the method according to the invention.
Figure 2:
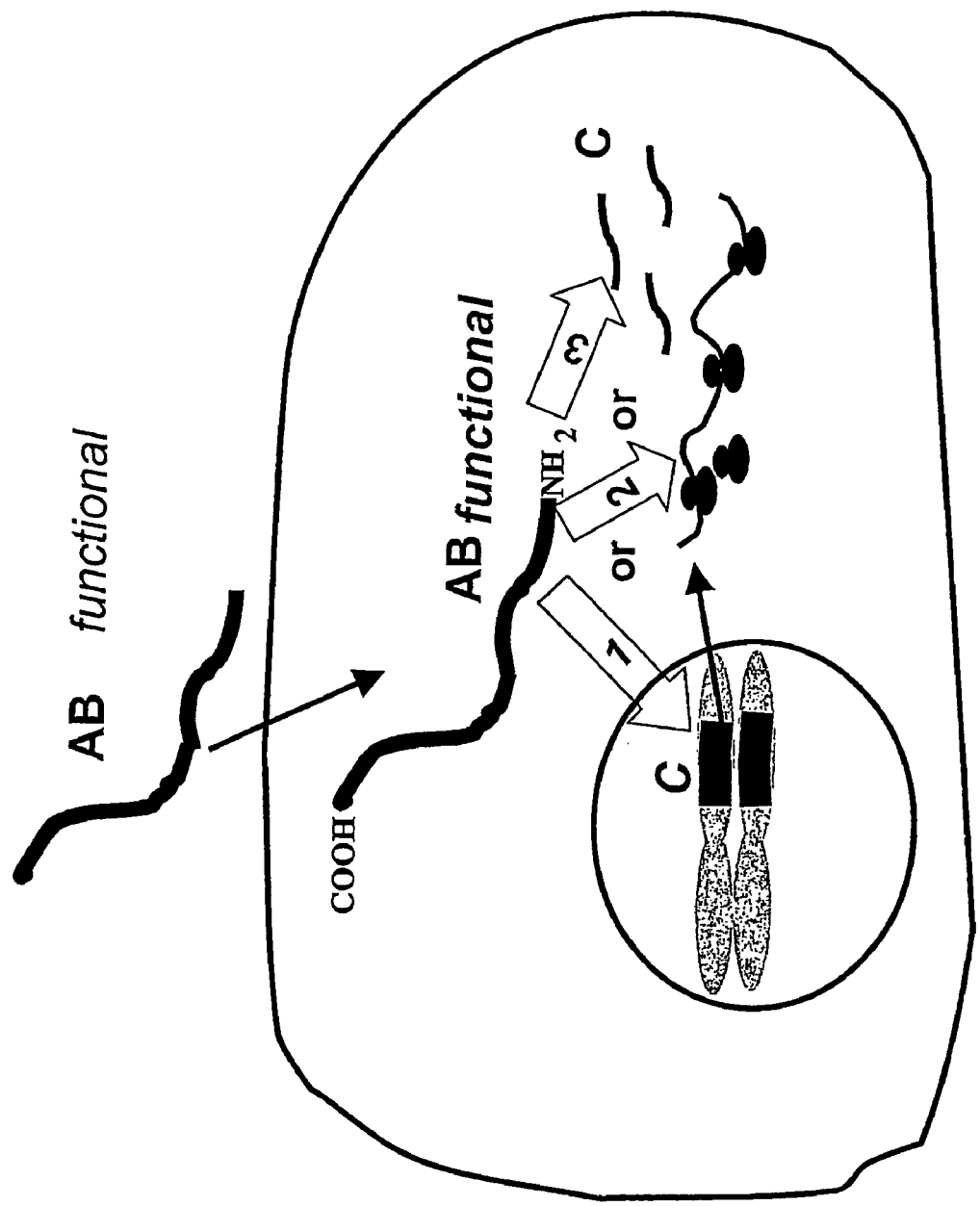
FIG. 2 is a schematic representation of a method according to the invention, wherein the polypeptide is an active (functional) protein (AB), C designates a heterologous DNA and its expression products (RNA or protein). RNA is indicated by having bound ribosomes. In the cell of a plant, the active protein (AB) can interact (1) with said heterologous nucleic acid, (2) with RNA expression products, or (3) with a protein expression product of said heterologous nucleic acid, for switching on a cellular process of interest.
Figure 3:
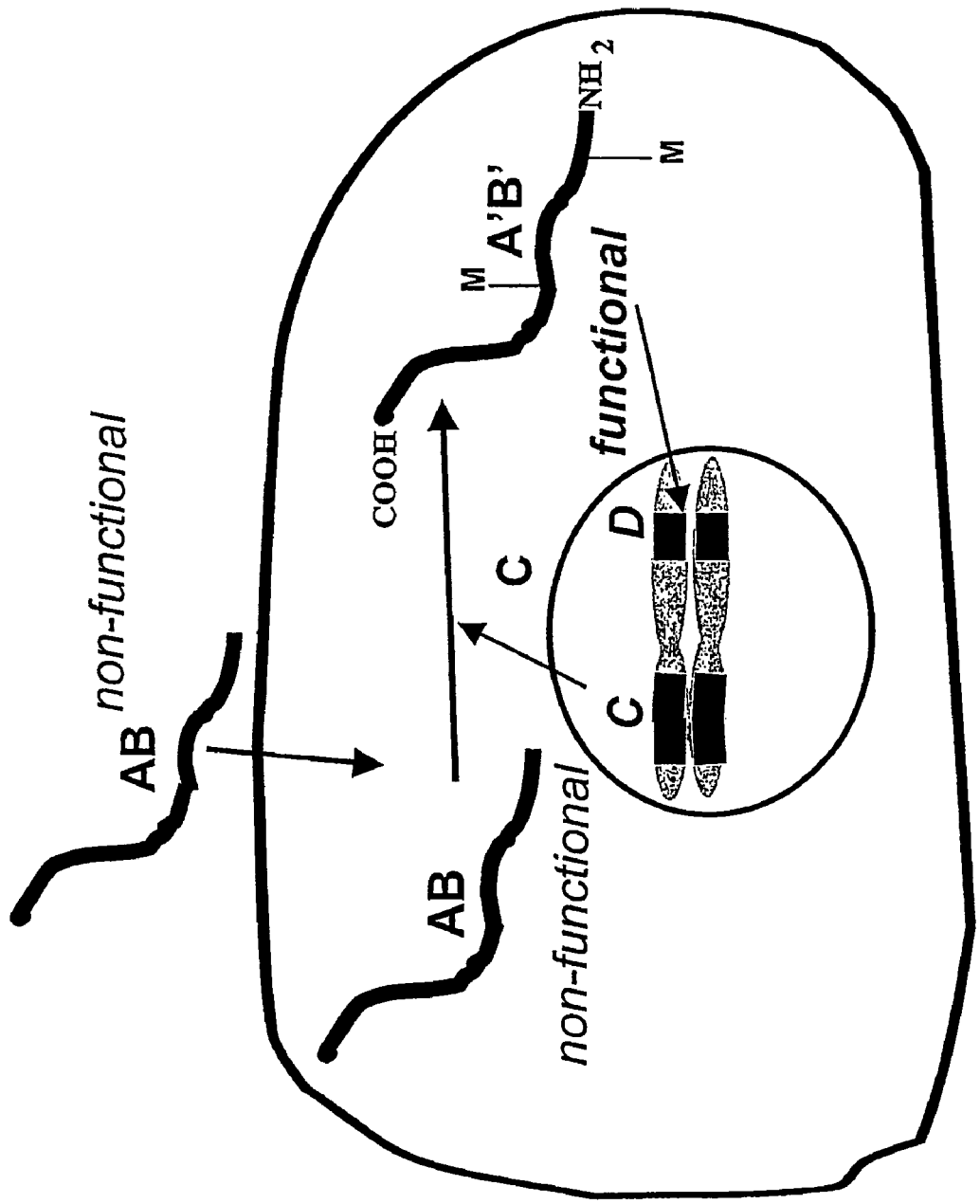
FIG. 3 is a schematic representation of a method according to the invention, wherein said polypeptide is a non-functional protein (AB) which after direct introduction into the plant cell is converted to an active form A'B' under the influence of a factor encoded by a heterologous nucleic acid C. D indicates an additional heterologous nucleic acid (or RNA or protein expression products thereof) that is targeted by the protein A'B', thus switching on a cellular process of interest. Said conversion to the active form A'B' may e.g. take place by an enzymatic activity of an expression product of C or by intein-mediated trans-splicing.

The same switching functions that are described herein for said protein switch may also be used for the switching function of said polypeptide and vice versa. There are countless numbers of cellular processes of interest which can be irreversibly triggered by said protein of the invention (protein switch). The protein switch (marked as AB in FIG. 2) can e.g. control the expression of a transgene of interest (designated C in FIG. 2) in many different ways. For example, it can trigger DNA recombination or transcription, RNA processing or translation, protein post-translational modifications (FIG. 2) etc. In addition, the protein switch can be activated by said polypeptide upon delivery into the plant cell and after that be able to function as a switch (FIG. 3). Obviously, the choice of the protein switch depends on the design/choice of the cellular process to be controlled in said plant. Said cellular process can be controlled, notably switched on, by nucleic add rearrangement or modification in cells wherein said protein is present or in cells that are invaded by said protein. In such case, the protein switch may comprise a DNA or RNA modifying enzyme like a site-specific endonuclease, a recombinase, a methylase, an integrase, a transposase, a polymerase etc. Other embodiments contemplated in this invention include triggering reactions such as DNA restriction and/or DNA replication. An example of a biochemical cascade that can be triggered by restriction is a two-component system wherein a DNA sequence containing an origin of replication and being integrated into a nuclear genome is specifically excised and converted into an autosomally replicating plasmid by a rare-cutting restriction enzyme serving as protein switch, thus triggering the cascade.

There are numerous reactions that affect RNA molecules that may be used as efficient triggering device for the cellular process according to the present invention. These include, inter alia, reactions such as RNA replication, reverse transcription, editing, silencing, or translation. There is abundant prior art describing in detail how, for example, a site-specific recombinase, integrase or transposase can trigger a process of interest by DNA excision, inversion or insertion in cells, notably in plant cells (Zuo, Moller & Chua, 2001, *Nat Biotech.*, 19, 157-161; Hoff, Schnorr & Mundy, 2001, *Plant Mol. Biol.*, 45, 41-49; U.S. Pat. No. 5,225,341; WO9911807; WO9925855; U.S. Pat. Nos. 5,925,808; 6,110,736 WO0140492; WO 0136595). Site-specific recombinases/integrases from bacteriophages and yeasts are widely used for manipulating DNA in vitro and in plants and animals. Preferred recombinases-recombination sites for the use in this invention are the following: Cre recombinase-LoxP recombination site, FLP recombinase-FRT recombination sites, R recombinase-RS recombination sites, phage C31 integrase recognising attP/attB sites etc. Transposons are widely used for the discovery of gene function in plants. Preferred transposon systems for use in the present invention include Ac/Ds, En/Spm, transposons belonging to the "mariner" family, etc.

Heterologous transcription factors and RNA polymerases may also be used in a protein switch according to the invention. For example, the delivery of T7 polymerase into cells of a plant carrying a transgene under the control of the T7 promoter may induce the expression of such a transgene.

The expression of a plant transgene (e.g. the additional heterologous nucleic acid of the invention) that is under control of a bacteriophage promoter (e.g. T3, T7, SP6, K11) with the corresponding DNA/RNA polymerase delivered into cells of a plant may be another efficient approach for the development of protein switches contemplated in this invention. Another useful approach may be the use of heterologous or chimaeric or other artificial promoters which require heterologous or engineered transcription factors for their activation. Heterologous transcription factors also can be used in order to induce expression of the transgene of interest under control of said transcription factor-recognizable promoter. Examples of such transcription factors are inter alia yeast metalloresponsive ACE1 transcription factor binding specific sequences in the yeast MT (metallothionein) promoter (Meft et al., 1993, *Proc. Natl. Acad. Sci.*, 90, 4567-4571), different chimaeric transcription factors having a sequence-specific DNA-binding domain and an activation domain like a transcription factor having a fusion six-zink finger protein 2C7 and herpes simplex virus VP16 transcription factor activation domain (Ordiz, Barbas & Beachy, 2002, *Proc. Natl. Acad. Sci. USA*, 99, 13290-13295), a transcription factor having a full length 434 repressor and the C-terminal 80 amino acids of VP16 transcriptional activator (Wilde et al., 1994, *Plant Mol. Biol.*, 24, 381-388), a transcription factor used in steroid-inducible systems (Aoyama & Chua, 1997, *Plant J.*, 11, 605-612; McNellis et al., 1998, *Plant J.*, 14, 247-257; U.S. Pat. No. 6,063,985) or a tetracycline-inducible system (Weinmann et al., 1994, *Plant J.*, 5, 559-569). In some cases, the existing inducible systems for transgene expression may be used. Alternatively, heterologous transcription factors may be modified such that no activating ligand-inducer will be required to drive the transcription factor into the active state. Chimaeric transcription factors would be of advantage for the use in this invention, as they allow to combine highly sequence-specific DNA binding domains and highly efficient activation domains, thus allowing a maximum desired effect after delivery of such a factor into the plant cell.

Another protein switch contemplated under the invention may rely on posttranslational modification of one or more expression product(s) of a heterologous nucleic acid, which may lead to the activation of the expression product. There are many possible implementations of such protein switches that could operate by controlling steps such as polypeptide folding, oligomer formation, removal of targeting signals, conversion of a pro-enzyme into an enzyme, blocking enzymatic activity, etc. For example, delivery of a site-specific protease into cells of a plant may trigger a cellular process of interest if a genetically-engineered host specifically cleaves a pro-enzyme, thus converting it into an active enzyme, if a product is targeted to a particular cellular compartment because of the host's ability to cleave or modify a targeting motif, or if a product is specifically mobilised due to the removal of a specific binding sequence. Cleavage of a translational fusion protein can be achieved via a peptide sequence recognized by a viral site-specific protease or via a catalytic peptide (Dolja et al., 1992, *Proc. Natl. Acad. Sci. USA*, 89 10208-10212; Gopinath et al., 2000, *Virology*, 267 159-173; U.S. Pat. No. 5,162,601; U.S. Pat. No. 5,766,885; U.S. Pat. No. 5,491,076). Other examples of site-specific proteases applicable to this invention are mammalian enterokinases, for example, human enterokinase light chain which recognizes the sequence DDDK-I (SEQ ID NO:1) (Kitamoto et al., 1994, *Proc. Natl. Acad. Sci.*, 91, 7588-7592), and specifically cleaves Lys-Ile bonds; viral proteases, like Hc-Pro (Carrington JC & Herndon KL,1992, *Virology*, 187, 308-315) which catalyzes proteolysis between the Gly-Gly dipeptide but requires 4 amino acids for the recognition of the cleavage site; site-specific protease of Semliki Forest Virus (Vasiljeva et al., 2001, *J Biol Chem.*, 276, 30786-30793); and proteases involved in polyubiquitin processing, ubiquitin-carboxy-terminal hydrolases (Osava et al., 2001, *Biochem Biophys Res Commun.*, 283, 627-633).

Directly Introducing Said Polypeptide into Cells of a Plant a) Microprojectile Bombardment (Particle Bombardment)

Different methods can be used for directly introducing (direct delivery) said polypeptide into cells of said plant. Among the simplest ones is the direct delivery with the help of mechanical interaction with plant tissue. For example, microprojectile bombardment of polypeptide-coated particles can deliver said polypeptide into the plant cell. The protocol can be similar to those described for DNA delivery in plant transformation protocols (U.S. Pat. No. 5,100,792; EP 00444882B1; EP 00434616B1). However, instead of DNA, said polypeptide may be used for coating the particles. There is a description of a biolistic process that uses particle coating methods which are reasonably gentle for preserving the activity of said polypeptide (Sanford, Smith & Russell, 1993, *Methods in Enzymol.*, 217, 483-509). In principle, other plant transformation methods can also be used e.g. microinjection (WO 09209696; WO 09400583A1; EP 175966B1), or liposome-mediated delivery (for review see: Fraley & Papahadiopoulos, 1982, *Curr. Top. Microbiol. Immunol.*, 96, 171-191).

b) Use of Membrane Translocation Amino Acid Sequences

The polypeptide of interest can be applied externally to target cells of said plant using a covalent fusion or non-covalent interaction with a membrane translocating sequence. Many examples of membrane translocating sequences (MTS), natural and synthetic, are known in the art. They are widely used as fusions with peptide drugs and therapeutic proteins in order to increase their cell membrane permeability. An MTS may be a simple amino acid repeat, for example a cationic peptide containing eleven arginines (SEQ ID NO:2) RRRRRRRRRRR (Matsushita et al., 2001, *J. Neurosci.*, 21, 6000-6007). Another cationic MTS is a 27 amino acid long transportan (SEQ ID NO:3) GWTLNSAGYL LGKINLKALA ALAKKIL (Pooga et al., 1998, *FASEB J.*, 12, 67-77). It is very likely that such peptides, for their penetration of the cell, exploit the asymmetry of the cellular plasma membrane where the lipid monolayer facing the cytoplasm contains anionic phospholipids (Buckland & Wilton, 2000, *Biochim. Biophys. Acta/Mol. Cell. Biol. Of Lipids*, 1483, 199-216). Certain proteins also contain subunits that enable their active translocation across the plasma membrane into cells. To such domains belongs the basic domain of HIV-1 Tat$_{49-57}$ (SEQ ID NO:4) (RKKRRQRRR) (Wender et al., 2000, *Proc. Natl. Acad. Sci. USA*, 97 13003-13008), Antennapedia$_{43-58}$ (SEQ ID NO:5) (RQIKIWFQNR RMKWKK) (Derossi et al., 1994, *J. Biol. Chem.*, 269, 10444-10450), the Kaposi Fibroblast Growth Factor MTS (SEQ ID NO:6) (AAVALLPAVL LALLAP) (Lin et al., 1995, *J. Biol. Chem.*, 270 14255-14258); the VP22 MTS (Bennet, Dulby & Guy, 2002, *Nat. Biotechnol.*, 20, 20; Lai et al., 2000, *Proc. Natl. Acad. Sci. USA*, 97, 11297-302); homeodomains from the *Drosophila melanogaster* Fushi-tarazu and Engrailed proteins (Han et al., 2000, *Mol Cells* 10, 728-732). It was shown that all these positively charged MTSs are able to achieve cell entry by themselves and as fusions with other proteins like GFP (Zhao et al., 2001, *J. Immunol. Methods*, 254, 137-145; Han et al., 2000, *Mol Cells*, 10, 728-732), Cre recombinase (Peitz et al., 2002, *Proc. Natl. Acad. Sci. USA*, 4489-4494) in an energy-independent manner. However, the fusion is not necessarily required for protein transport into the cell. A 21-residue peptide carrier Pep-1 was designed (SEQ ID NO:7) (KETWWETWWTEWSQPKKKRKV) which is able to form complexes by mean of non-covalent hydrophobic interactions with different types of proteins, like GFP, b-Gal, or full-length specific antibodies. These complexes are able to efficiently penetrate cell membranes (Morris et al., 2001, *Nature Biotechnol.*, 19, 1173-1176). The list of MTS can be continued and, in general, any synthetic or naturally occurring arginine-rich peptide can serve for practicing this invention (Futaki et al., 2001, *J. Biol. Chem.*, 276, 5836-5840).

As there is no essential structural difference between plant and animal cell membranes affecting their general architecture and physico-chemical properties, said fusions of MTS with said polypeptide of the invention can also be efficiently used for penetrating plant cells. However, unlike animal cells, plant cells possess a tough cell wall (Varner & Linn, 1989, *Cell*, 56, 231-239; Minorsky, 2002, *Plant Physiol.*, 128, 345-53). This obstacle can be overcome by using simple techniques. For example, injection of a (e.g. crude) protein extract containing said polypeptide having an MTS into a plant apoplast facilitates translocation of said polypeptide into the plant cells. Another approach to overcome the cell wall and to reach the cell membrane of plant cells can be the application of cellulytic enzymes many of which are commercially available. Once added to a composition containing said polypeptide, said enzymes help to remove or weaken the cell wall, but will leave the cell membrane intact and exposed for penetration by said polypeptide containing said MTS. Said cellulytic enzymes from bacteria and molds have been commercially available at industrial scale for a long time and are widely used (e.g. "Onozuka" R-10 enzyme preparation of *Trichoderma harzianum*, etc.) in plant cell tissue culture for obtaining plant protoplasts (Sidorov &Gleba, 1979, *Tsitologia*, 21, 441-446; Gleba & Gleba, 1978, *Tsitol Genet*, 12, 458-469; Ghosh et al., 1994, *J. Biotechnol.*, 32, 1-10; Boyer, Zaccomer & Haenni, 1993, *J. Gen. Virol*, 74, 1911-1917; Hilbricht, Salamini & Bartels, 2002, Plant J., 31, 293-303). The approach of using cellulytic enzymes has potential for large scale applications of this invention. A mixture of cellulytic enzymes with a cell-permeable polypeptide can be sprayed over the genetically-modified plants or over parts thereof. Cellulases can make cell membranes accessible for membrane permeable polypeptides. Upon translocation into the cell, said polypeptide may trigger said cellular process of interest and the expression of said protein within the plant.

In addition to the above delivery methods for said polypeptide, efficient spreading of a protein switch inside the plant is preferably used for amplification purposes within said plant. Further, to make the overall method safe, strict control over the heterologous nucleic acid is required.

Figure 4:
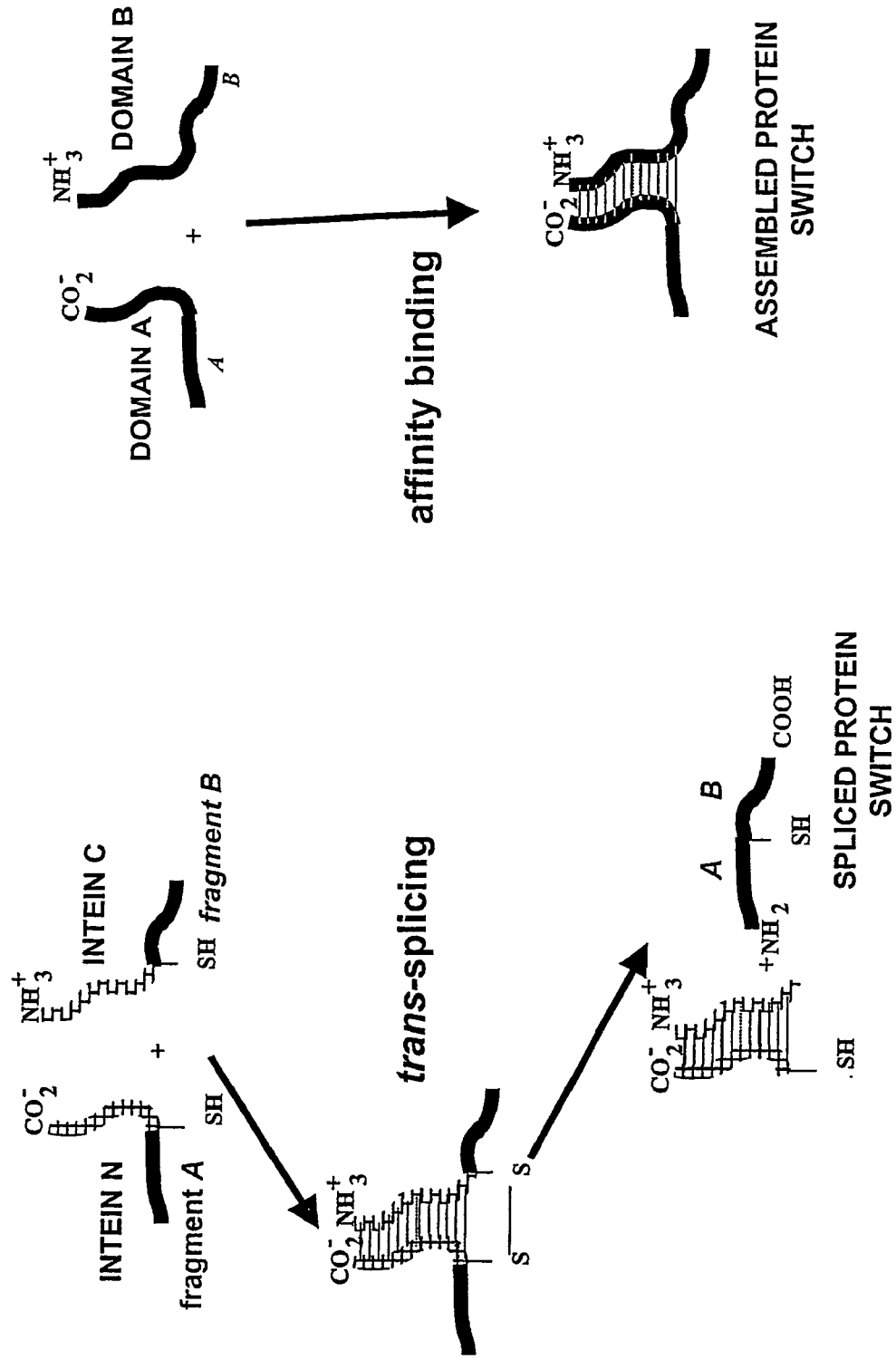
FIG. 4 is a scheme showing embodiments for generating an active protein switch from inactive protein fragments in a plant cell. A: generation of an active protein switch by intein-mediated trans-splicing of protein fragments. B: generation of an active protein switch by affinity binding of protein fragments.
Figure 5:
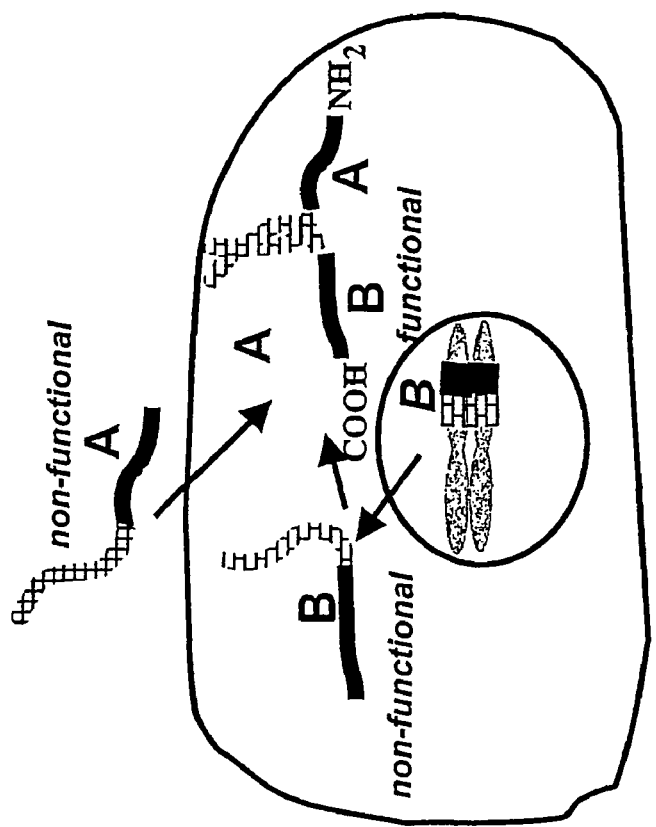
FIG. 5 is a scheme showing assembly of a functional protein (AB) from non-functional protein fragments A and B by intein-mediated trans-splicing (FIG. 5A) or affinity interaction (FIG. 5B). Fragment A is the polypeptide of the invention that is imported into the cell. Fragment B is internally expressed from a heterologous nucleic acid.
Figure 5:
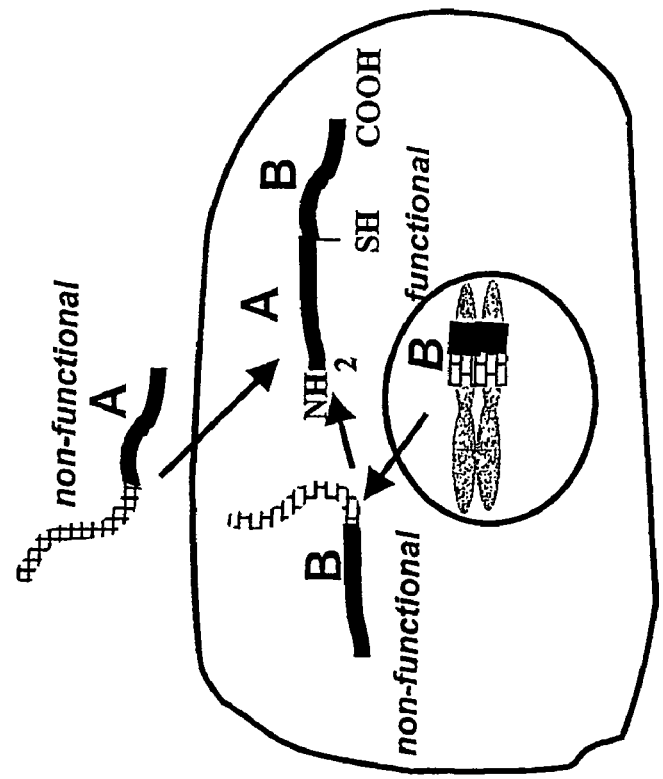
Figure 6:
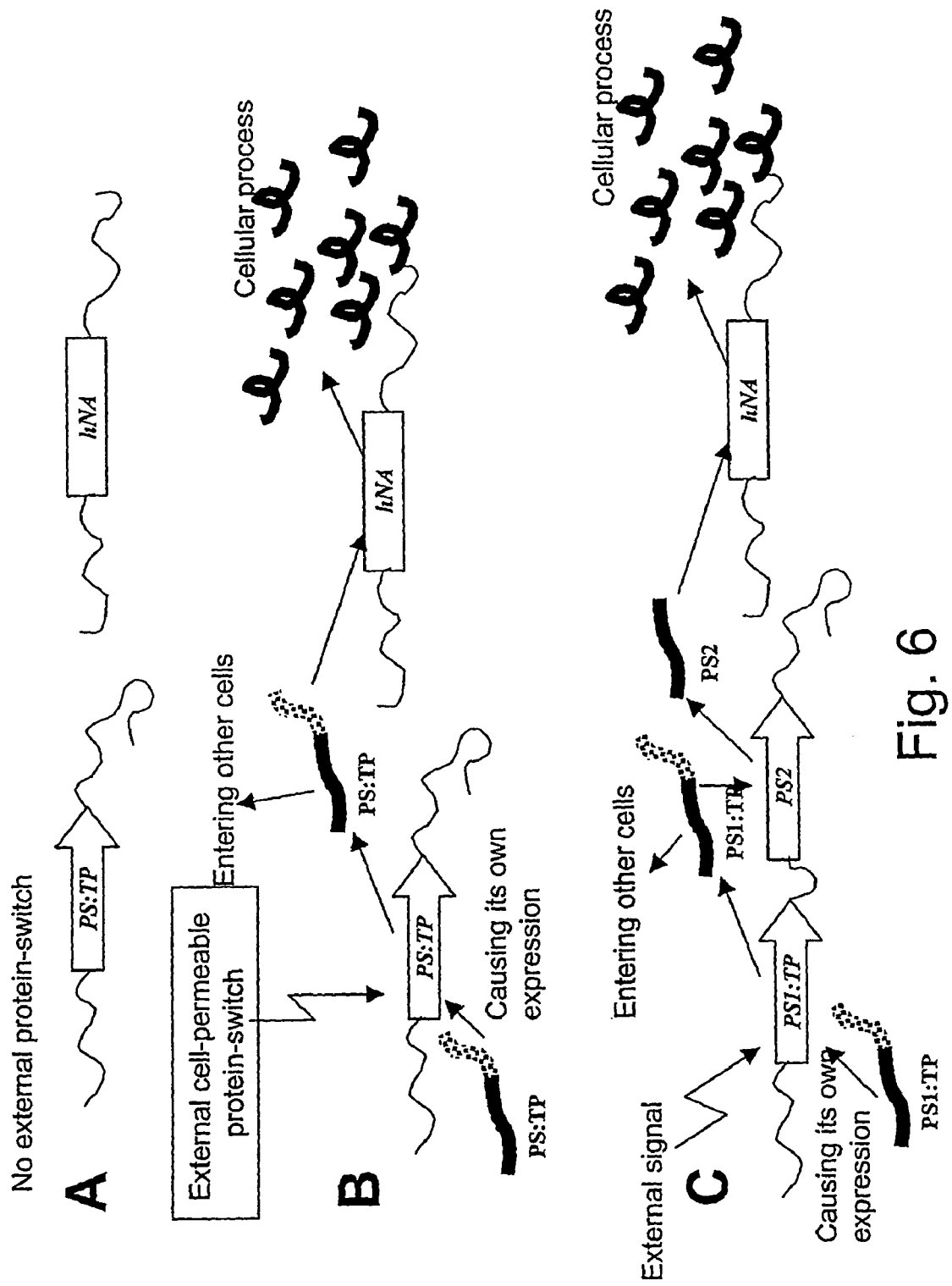

In order to address these issues it is proposed herein to use a "split genes" (or "split proteins") approach for controlling the segregation of a transgene encoding the protein switch. In this embodiment, an active (functional) protein switch is assembled either by intein-mediated protein trans-splicing (FIG. 4-A and FIG. 5-A) or by affinity interaction (FIG. 4-B and FIG. 5-B). In this case, the protein switch is not encoded by a continuous DNA sequence and its use may be much better controlled. Such an active protein switch may e.g. be assembled from said polypeptide and a protein expressed in cells of said plant (e.g. from the heterologous nucleic acid) by intein-mediated protein trans-splicing or by affinity interaction. The protein expressed from said heterologous nucleic acid and said polypeptide may jointly generate a predetermined function leading to switching on said cellular process of interest only when the protein and said polypeptide are jointly present. The protein expressed from said heterologous nucleic acid may e.g. be constitutively expressed, whereby the process of interest can be switched by applying said polypeptide. Alternatively, the protein expressed from said heterologous nucleic acid may be under the control of a regulated promoter (e.g. a chemically inducible promoter), which allows a "double" control of the process of interest, namely by induction of the regulated promoter and the introduction of said polypeptide. Importantly, these embodiments have an exceptional biological safety. Intein-mediated protein trans-splicing and affinity interaction are described next.

Intein-mediated trans-splicing of proteins with restoration of their activity is known in the prior art and is described in detail in many publications. Protein affinity interaction and/or trans-splicing can be achieved by using engineered inteins (FIG. 4-A). Inteins were first identified as protein sequences embedded in-frame within protein precursor and excised during protein maturation process (Perler et al., 1994, Nucleic Acids Res., 22, 1125-1127; Perler, F. B., 1998, Cell, 92, 14). All information and catalytic groups necessary to perform a self-splicing reaction reside in the intein and two flanking amino acids. The chemical mechanism of protein splicing is described in detail by Perler and colleagues (1997, Curr. Opin. Chem. Biol., 1, 292-299) and by Shao & Kent (1997, Chem. Biol., 4, 187-194). Inteins usually consist of N- and C-terminal splicing regions and a central homing endonuclease region or small linker region. Over 100 inteins are known so far that are distributed among the nuclear and organellar genomes of different organisms including eukaryotes, archaebacteria and eubacteria (www.neb.com/neb/inteins.html). It was shown that inteins are capable of trans-splicing. The removal of the central homing endonuclease region does not have any effect on intein self-splicing. This made possible the design of trans-splicing systems, in which the N-terminal and C-terminal fragments of an intein are co-expressed as separate fragments and, when fused to exteins (protein fragments that are ligated together with the help of the intein), can perform trans-splicing in vivo (Shingledecker et al., 1998, Gene, 207, 187-195). It was also demonstrated with N- and C-terminal segments of the *Mycobacterium tuberculosis* RecA intein, that protein trans-splicing can take place in vitro (Mills et al., 1998, Proc. Natl. Acad. Sci. USA, 95, 3543-3548). This phenomenon was also identified for the DnaE protein of *Synechocystis* sp. strain PCC6803 (Wu et al., 1998, Proc. Natl. Acad. Sci. USA, 95, 9226-9231). Two different genes located more than 700 Kb.p. apart on opposite DNA strands encode this protein. It was also shown that two intein sequences encoded by those genes reconstitute a split mini-intein and are able to mediate protein trans-splicing activity when tested in *Escherichia coli* cells. An intein of the same origin (DnaE intein from *Synechocystis* sp. strain PCC6803) was used to produce functional herbicide-resistant acetolactate synthase II from two unlinked fragments (Sun et al., 2001, Appl. Environ. Microbiol., 67, 1025-29) and 5-enolpyruvylshikimate-3-phosphate synthase (EPSPS) (Chen et al., 2001, Gene, 263, 3948) in *E. coli*.

Trans-splicing of protein fragments (including covalent bond formation between exteins) is not necessarily required to restore the original function of the split protein. In many cases, affinity interaction between protein parts without peptide bond formation is sufficient to restore protein function (FIG. 4-B). This approach is most successful (as in case of intein-mediated trans-splicing) with proteins having two or more functional domains. In this case, the domains can be separated from each other by splitting the coding sequence between two transcription vectors and can be brought together by protein-mediated affinity interactions (FIG. 5-B). Protein domains can interact without the necessity to use interacting inteins. There is an example of reconstituting activity of the IS10 transposase consisting of two structural domains connected by a proteolysis-sensitive linker region (Kwon, Chalmers & Kleckner, 1995, Proc. Natl. Acad. Sci. USA, 92, 8234-8238). Each of the domains separately is unable to provide the transposase function. When added together, however, they are able to provide for transpositions even without being connected by a linker region. There are many other examples of the reconstitution of functional proteins from isolated fragments without peptide bond formation. The efficient assembly of a functional insulin receptor binding site was achieved by simple mixing of non-functional fragments (Kristensen et al., 2002, J. Biol. Chem., 277, 18340-18345). Reconstitution of active proteins by simple mixing of two inactive peptide fragments was shown for leucine dehydrogenase (Oikawa et al., 2001, Biochem. Biophys. Res. Commun., 280, 1177-1182), $Ca^{2+}$-binding protein calbindin D28k (Berggard et al., 2000, Protein Sci., 9, 2094-2108; Berggard et al., 2001, Biochemistry, 40, 1257-1264), *Arabidopsis* developmental regulator COP1 (Stacey et al., 2000, Plant Physiol., 124, 979-990), diopamine D receptor (Scarselli et al., 2000, Eur. J. Pharmacol, 397, 291-296), microplasminogen (De Los Santos, Wang & Reich, 1997, Ciba Found. Symp., 212, 76-83) and many others.

Leucine zipper domains are of special interest for forming protein heterodimers once fused to a protein of interest (Riecker & Hu, 2000, Methods Enzymol., 328, 282-296; Liu et al., 2001, Curr. Protein Pept. Sci., 2, 107-121). An interesting example is the control of protein-protein interactions with a small molecule. For example, Cre recombinase was engineered in such a way that, when split in two inactive fragments, was able to restore 100% of its recombinase activity in the presence of the small molecule rapamycin that triggered activity complementation by heterodimerization between two inactive fragments (Jullien et al., 2003, Nucleic Acids Res., 31, e131). Rapamycin and, preferably non-toxic, analogues can also be used for conditional protein splicing, where they trigger a trans-splicing reaction (Mootz et al., 2003, J. Am. Chem. Soc., 125, 10561-10569). Similar approaches for regulation of protein-protein interactions with the help of small molecules, such as rapamycin or rapamycin analogues, are described in several papers (Amara et al., 1997, Proc. Natl. Acad. Sci. USA., 94, 10618-10623; Pollock et al., 2000, Proc. Natl. Acad. Sci. USA., 97, 13221-13226; Pollock et al., 2002, Nat. Biotechnol., 20, 729-733). Many other chemical dimerizers such as dexamethasone and methotrexate, can be used for assembling active homo- or heterodimers from inactive protein fragments (for review see: Pollock & Clackson, 2002, Curr. Opin. Biotechnol., 13, 459-467).

Affinity interactions can be efficiently engineered by using naturally occurring interacting protein domains or by identifying such domains with the help of two-hybrid (Fields & Son, 1989, *Nature*, 340, 245-246; Chien et al., 1991, *Proc. Natl. Acad. Sci. USA*, 88, 9578-9582; *Yeast Protocol Handbook*, Clontech Laboratories, Inc., 2000) or phage display systems. For example, phage display may be used to select a 5-12-mer oligopeptide with high affinity to a protein fragment of interest. Several such systems are now commercially available. Phage display is a selection technique in which a short variable 5-12-mer oligopeptide is inserted into a coat protein of bacteriophage. The sequence encoding this variable oligopeptide is included in the corresponding gene of the bacteriophage coat protein. Usually, a 7-mer phage display library has at least $10^9$ independent clones bearing different combinations of 7-mer amino acids in variable oligopeptides. Phage display has been used to create affinity complexes between bacteriophage and a protein of interest, allowing rapid identification of peptide ligands for a given target protein by an in vitro selection process called "panning" (Parmley, Smith, 1988, *Gene* 73, 305-318; Cortese et al., 1995, *Curr. Opin. Biotechnol.*, 6, 73-80). The phage-protein complex created after the panning procedure can be dissociated and a phage with affinity to a target protein can be amplified. Usually, one needs three panning cycles to get bacteriophage with high affinity. After three rounds, individual clones can be characterized by sequencing of variable region in genomic DNA. Said system can be efficiently adopted for identifying short interacting oligopeptides and using them as affinity tags in order to bring together protein fragments.

Another approach includes the use of naturally occurring interacting domains like leucine-rich repeats (Kobe & Deisenhofer, 1994, *Trends Biochem Sci.*, 19, 415-421; Kobe & Kajava, 2001, *Curr. Opin. Struct. Biol.*, 11, 725-732), zinc finger (Grossley, Merika & Orkin, 1995, *Mol. Cell. Biol.*, 15, 2448-2456), ankyrin repeats (Thompson, Brown & McKnight, 1991, *Science*, 253, 762-768), chromo domains (Paro & Hogness, 1991, *Proc. Natl. Acad. Sci. USA*, 88, 263-267; Singh et al., 1991, *Nucleic Acids Res.*, 19, 789-793) and many others involved in protein-protein interactions. However, the possibility of involving not only the engineered protein fragments containing the motive fusions in protein-protein interactions, but also endogenous proteins can be taken into account.

Involving protein-protein interactions for switching on a cellular process of interest like gene expression has inter alia the following advantages: Firstly, the system may be rendered highly specific, as the function of interest is a result of a highly specific protein-protein or protein-nucleic acid interaction, which is characterized by zero-level uninduced state and absence of non-specific leakiness. This is in contrast to prior art systems such as switches based on small molecules that are inherently less specific and invariably show a certain degree of leakiness. Secondly, said protein switch or a fragment thereof (or said polypeptide or a fragment thereof can be directly delivered into cells of a plant without a nucleic acid vector encoding said polypeptide, thus allowing precise dosage of said polypeptide. This makes direct delivery of said protein switch (or said polypeptide) into cells of a plant comparable with the use of small molecules for triggering a required process in cells. Thirdly, the system is inherently environmentally safer than prior art systems that contain full genetic information for the protein of interest (either in a form of linear nucleic acid or fragments of said nucleic acid), since it allows that the organism in question does not contain the full genetic information necessary for the expression of a protein of interest. According to the central dogma of molecular biology, biological systems cannot reverse translate proteins to nucleic acids. Thus, the 'reverse engineering' of the genetic information sufficient for expression of a functional trait by a living organism is impossible. Fourthly, the system provides a specific lock that could be used to prohibit unauthorized use of the system. The use of said polypeptide as a component of a crude protein extract from organism expressing said polypeptide or said polypeptide fragment makes it practically very difficult to identify the active component of said extract.

Spread of the Protein Switch within a Plant for Triggering a Cellular Process of Interest Here, an approach for overcoming the problem of the low number of cells of a plant that can be reached by the externally-applied polypeptide is provided: said polypeptide may lead to the formation of an intracellular protein-switch molecule capable of cell-to-cell or systemic movement. Moreover, said polypeptide may lead to or may cause the formation of a virus-based vector (amplicon) expressing a gene of interest or a part thereof and being capable of cell-to cell or systemic movement in said plant. In these approaches, the movement of either viral vectors- or protein-switch molecules or both can lead to the spread of a cellular process and/or biochemical cascade over significant parts of said plant and even all over the genetically-modified plant.

Figure 7:
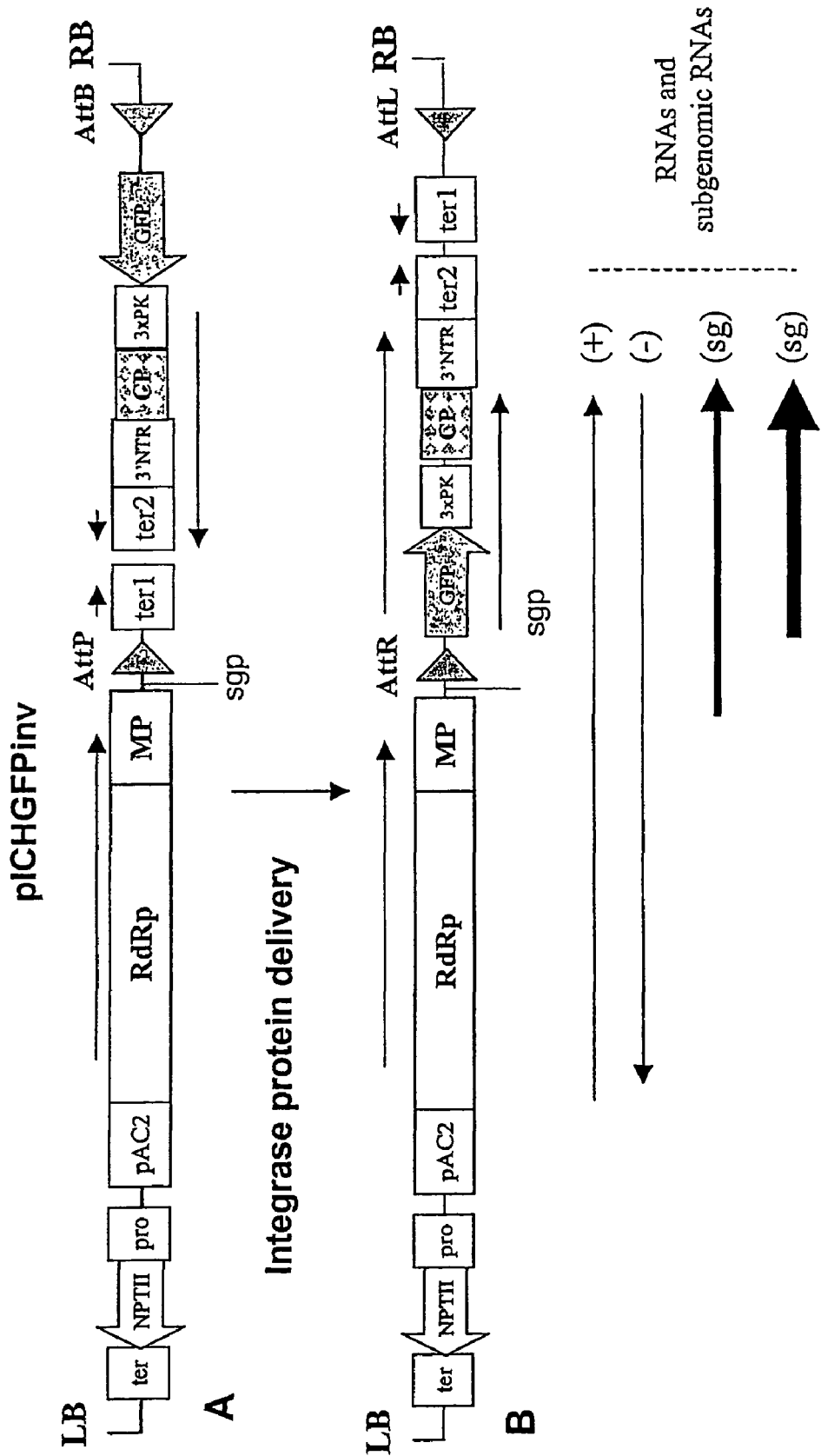
Figure 8:
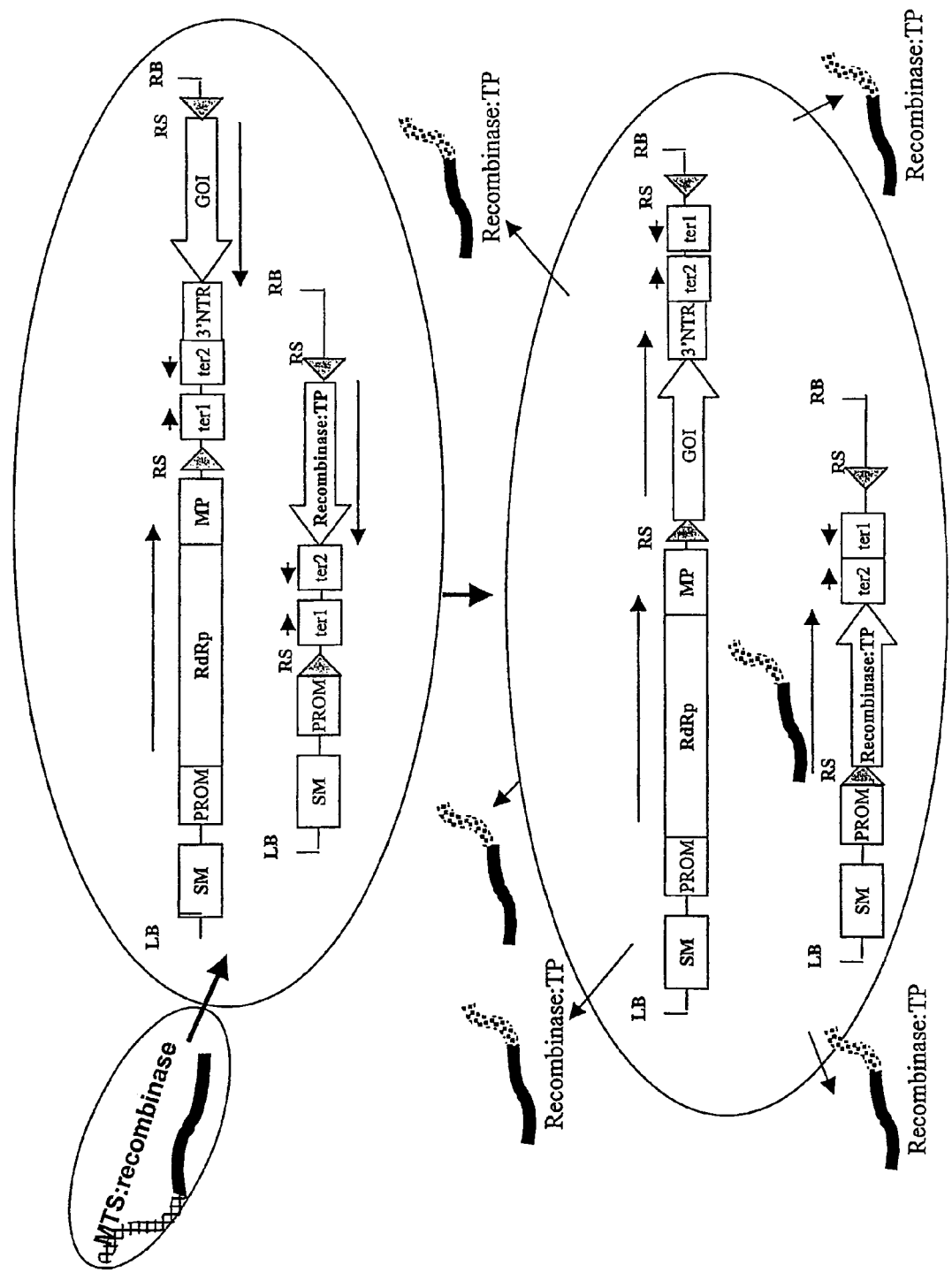

In Example 1 of this invention, the protein-switch contains an integrase phiC31 to convert a precursor vector of a viral vector into the viral vector. The viral vector is capable of amplification, cell-to-cell and systemic movement. Integrase-mediated recombination between attP and attB sites of pICH-GFPinv (FIG. 7-A) leads to the inversion of a DNA fragment flanked by said sites and formation of a viral vector capable of amplification and expression of gene of a interest (GFP) (FIG. 7-B). This may be achieved as the result of placing viral components (3'NTR-3' non-translated region; CP—coat protein) necessary for vector amplification and systemic transport in sense orientation relative to a promoter active in the plant in question like the actin 2 promoter in this example. Thus, together with other viral vector components (e.g. RdRp and CP) it may form a cDNA which upon actin 2 promoter-driven transcription forms an RNA viral vector capable of amplification, cell-to-cell and systemic movement. Optionally, said vector can be further modified by removing the CP (coat protein) gene. Such a vector lacking the CP gene will still be capable of cell-to-cell movement. The construction of plant virus-based expression systems for the expression of non-viral genes in plants has been described in several papers (Dawson et al., 1989, *Virology*, 172, 285-293; Brisson et al., 1986, *Methods in Enzymology*, 118, 659; MacFarlane & Popovich, 2000, *Virology*, 267, 29-35; Gopinath et al., 2000, *Virology*, 267, 159-173; Voinnet et al., 1999, *Proc. Natl. Acad. Sci. USA*, 96, 14147-14152) and reviews (Porta & Lomonossoff, 1996, *Mol. Biotechnol.*, 5, 209-221; Yusibov et al., 1999, *Curr. Top. Microbiol. Immunol.*, 240, 81-94) and can be easily performed by those skilled in the art. Viral vector-based expression systems offer a significantly higher yield of a transgene product compared to plant nuclear transgenes. For example, the level of a transgenically encoded protein can reach 5-10% of the total cellular plant protein content when expressed from a viral vector (Kumagai et al., 2000, *Gene*, 245, 169-174; Shivprasad et al., 1999, *Virology*, 255, 312-323). RNA viruses are the most suitable as they offer a higher expression level compared to DNA viruses. There are several published patents which describe viral vectors suitable for systemic expression of transgenic material in plants (U.S. Pat. No. 5,316,931; U.S. Pat. No. 5,589,367; U.S. Pat. No. 5,866, 785). In general, these vectors can express a foreign gene as a translational fusion with a viral protein (U.S. Pat. No. 5,491, 076; U.S. Pat. No. 5,977,438), from an additional subgenomic promoter (U.S. Pat. No. 5,466,788; U.S. Pat. No. 5,670,353; U.S. Pat. No. 5,866,785), or from polycistronic viral RNA using IRES (internal ribosome entry site) elements for independent protein translation (German Patent Application DE 10049587). The first approach—translational fusion of a recombinant protein with a viral structural protein (Hamamoto et al., 1993, BioTechnology, 11, 930-932; Gopinath et al., 2000, Virology, 267, 159-173; JP6169789; U.S. Pat. No. 5,977,438) gives significant yield of a recombinant protein product. However, the usefulness of this approach is limited, as the recombinant protein cannot be easily separated from the viral one. An alternative of this approach employs a translational fusion via a peptide sequence recognized by a viral site-specific protease or via a catalytic peptide (Dolja et al., 1992, Proc. Natl. Acad. Sci. USA, 89, 10208-10212; Gopinath et al., 2000, Virology, 267, 159-173; U.S. Pat. No. 5,162, 601; U.S. Pat. No. 5,766,885; U.S. Pat. No. 5,491,076). Expression processes utilizing viral vectors built on heterologous subgenomic promoters provide the highest level of protein production to date (U.S. Pat. No. 5,316,931). The most serious disadvantage of viral vectors and many others is their limited capacity with regard to the size of DNA to be amplified. Usually, stable constructs accommodate inserts of not more than one kb. In some areas of plant functional genomics this may not be such a serious limitation, as G. della-Cioppa et al. (WO993651) described the use of TMV-based viral vectors to express plant cDNA libraries with the purpose of silencing endogenous genes. Two-component amplification systems which make use of helper viruses may offer a slightly better capacity (U.S. Pat. No. 5,889,191). Other systems based on expression cassettes that are stably integrated into the plant genome contain the strong 35S promoter driving the expression of viral vector based amplicons. These systems usually are subject to post-transcriptional gene silencing (PTGS) (Angell & Baulcombe, 1997, EMBO J., 16, 3675-3684). The use of PTGS suppressors is necessary to overcome such silencing (WO0138512). It requires to perform crosses between plants carrying the silenced amplicon and plants carrying the source of PTGS suppressor (Mallory et al., 2002, Nature Biotechnol, 20, 622-625) for achieving large scale production of a protein of interest with the help of such system. Evidently, such a system has no flexibility and no tight control over transgene expression and is restricted to the production of proteins which do not compromise plant growth and development.

Our approach allows to overcome the limitations of the above-described viral vector systems, specifically their limited capacity for the size of the gene to be expressed and the lack of flexibility in controlling the expression. In our invention, the viral vector precursor (also referred to as provector) is preferably present in each cell of the transgenic plant. In the case of expression of large genes (above 1 Kb), protein-switch movement is preferred over viral vector movement. Viral vectors can efficiently amplify in cells and the size of the insert of a viral vector mostly affects the ability for cell-to-cell and systemic movement. Therefore, providing a moveable protein switch capable of activating a viral vector to many cells or even to all cells of the host plant will solve the above-mentioned problem. Additionally, to provide a system with an efficient switching function that is able to turn on the amplification of such a viral vector in most if not all cells of the host plant, protein switches capable of cell-to-cell/systemic movement are used in the present invention.

To this end, the protein switch may contain a protein portion that renders said protein capable of cell-to-cell and/or systemic movement. Examples of such protein portions capable to intercellular trafficking are known in prior art. There is evidence that plant transcription factors, defence-related proteins and viral proteins can traffic through plasmodesmata (for review see: Jackson & Hake, 1997, *Curr. Opin. Genet. Dev.,* 7, 495-500; Ding, B. 1998, *Plant Mol. Biol.,* 38, 279-310; Jorgensen R A., 2000, *Sci STKE,* 58, PE2; Golz & Hudson, 2002, *Plant Cell,* 14, S277-S288). It was shown that a fusion of 3a movement protein of Cucumber mosaic virus with GFP can traffic out via plasmodesmata to neighboring cells (Itaya et al., 2002, *Plant Cell,* 14, 2071-2083). Such fusions also showed movement through phloem from transgenic rootstock into non-transgenic scion. The movement protein of tobacco mosaic virus (TMV), P30, traffics between cells through plasmodesmata and, by affecting plasmodesmata size, facilitates the movement of many other large macromolecules not specified for such movement (Citovsky et al., 1999, *Phil. Trans. R Soc. London B Biol Sci.,* 354, 637-443; Ding, Itaya & Woo, 1999, *Int Rev. Cytol.,* 190, 251-316). The P30:GFP fusion showed movement between the cells independent of physiological conditions, while the non-targeted GFP diffusion through plasmodesmata at large depends of physiological state of the plant cells (Crawford & Zambryski, 2001, *Plant Physiol,* 125, 1802-1812). The fusion of GFP with transcription factor knotted1 also showed the ability for intercellular trafficking. The GFP:KN1 fusion protein demonstarted movement from internal tissues of the leaf to the epidermis, between epidermal cells and into the shoot apical meristem of tobacco plant (Kim et al., 2002, *Proc. Natl. Acad. Sci. USA,* 99, 4103-4108). Plasmodesmata play an important role in such trafficking and its physiologigal stage and structure are important for the efficiency of such trafficking. For example, simple plasmodesmata allow the nonspecific trafficking of proteins in developing tobacco leaves, while the branched ones do not (Oparka et al., 1999, *Cell,* 98, 5-8). Allowing trafficking of macromolecules including proteins appears to be a normal function of plasmodesmata, which was made use of by plant viruses for their cell-to-cell spread (Fujiwara et al., 1993, *Plant Cell,* 5, 1783-1794). In general, it is evident that plasmodesmata and the phloem play an important role in the transport and delivery of information macromolecules (proteins and nucleic acids) (Ruiz-Medrano et al., 2001, *Curr. Opin. Plant Biol.,* 4, 202-209). Phloem sap proteins from *Cucurbita maxima* and *Ricinum communis* have the capacity of cell-to-cell trafficking through plasmodesmata (Balachandran et al., 1997, *Proc. Natl. Acad. Sci. USA.,* 94, 14150-14155).

FIG. 8 shows schematically possibilities of achieving intercellular movement of the protein switch of the invention. An externally-delivered protein switch (i.e. said polypeptide) and the protein switch synthesised within a cell can be fusions of the same or different protein segments to translocating or trafficking signals. In our example (FIG. 8), the same protein segment, e.g. a recombinase is fused either with a membrane translocating signal (MTS) for cell membrane permeability to form said polypeptide of the invention, or with a protein portion (TP) providing for intercellular trafficking to form said protein switch. It is very likely that for small proteins (like GFP and smaller), fusion to TP might not be necessary, as they may be capable of highly efficient cell-to-cell movement by simple diffusion. However, for larger protein switches, fusion with a TP or an active fragment thereof is advantageous. It is evident that among all proteins involved in intercellular trafficking, viral proteins are studied the best. They are the most preferred candidates to be included in a protein switch. As is shown in FIG. 8, an externally delivered polypeptide may trigger the expression of a transgene encoding a protein switch having the same enzymatic activity, but that is capable of intercellular trafficking (recombinase:TP).

Said protein switch capable of trafficking may trigger protein switch expression in all affected cells, what represents a chain reaction. Availability of said protein switch in the cell is a prerequisite for triggering the expression of a gene of interest (GOI) in cells by DNA rearrangement, causing viral vector-based amlicon formation. The size of the gene of interest expressed from such an amplicon is not a limiting factor for efficient GOI expression, since amplicon stability and cell-to-cell movement are not necessary in this system: the viral provector may be present in each plant cell and the spreading of the protein-switch may trigger the expression of the gene of interest in each of these cells. Preferably, however, spreading of the amplicon contributes to efficient GOI expression.

The ultimate purpose of the protein switch system contemplated herein is an operational control of a cellular process of interest or a cascade of biochemical reactions of interest in a plant production system. A biochemical cascade is a chain of biochemical reactions in a host production system that ultimately yields a specific product, effect, or trait of interest.

The approaches described herein, in addition to being versatile and leakage-proof, provide an efficient production control method. The two-component process described above is in essence a "key-lock" system, whereby a company can efficiently control access to production by selling the protein-switch component.

Preferred plants for the use in this invention include any plant species with preference given to agronomically and horticulturally important species. Common crop plants for the use in present invention include alfalfa, barley, beans, canola, cowpeas, cotton, corn, clover, lotus, lentils, lupine, millet, oats, peas, peanuts, rice, rye, sweet clover, sunflower, sweetpea, soybean, sorghum triticale, yam beans, velvet beans, vetch, wheat, wisteria, and nut plants. The plant species preferred for practicing of this invention are including but not restricted to: representatives of Gramineae, Compositeae, Solanaceae and Rosaceae, whereby Solanaceae are preferred.

Additionally, preferred species for use the invention, as well as those specified above, plants from the genera: *Arabidopsis, Agrosts, Allium, Antirrhinum, Apium, Arachis, Asparagus, Atropa, Avena, Bambusa, Brassica, Bromus, Browaalia, Camellia, Cannabis, Capsicum, Cicer, Chenopodium, Chichorium, Citrus, Coffea, Coix, Cucumis, Curcubita, Cynodon, Dactylis, Datura, Daucus, Digitalis, Dioscorea, Elaeis, Eleusine, Festuca, Fragaria, Geranium, Glycine, Helianthus, Heterocallis, Hevea, Hordeum, Hyoscyamus, Ipomoea, Lactuca, Lens, Lilium, Linum, Lolium, Lotus, Lycopersicon, Majorana, Malus, Mangifera, Manihot, Medicago, Nemesia, Nicotiana, Onobrychis, Oryza, Panicum, Pelargonium, Pennisetum, Petunia, Pisum, Phaseolus, Phleum, Poa, Prunus, Ranunculus, Raphanus, Ribes, Ricinus, Rubus, Saccharum, Salpiglossis, Secale, Senecio, Setaria, Sinapis, Solanum, Sorghum, Stenotaphrum, Theobroma, Trifolium, Trigonella, Triticum, Vicia, Vigna, Vitis, Zea*, and the Olyreae, the Pharoideae and many others.

Within the scope of this invention the plant species, which are not included into the food or feed chain are specifically preferred for pharmaceutical and technical proteins production. Among them, *Nicotiana* species are the most preferred, as the species easy to transform and cultivate with well developed expression vectors (especially viral vectors) systems.

Genes of interest, their fragments (functional or non-functional) and their artificial derivatives that can be expressed as the cellular process of interest and isolated using the present invention include, but are not limited to: starch modifying enzymes (starch synthase, starch phosphorylation enzyme, debranching enzyme, starch branching enzyme, starch branching enzyme II, granule bound starch synthase), sucrose phosphate synthase, sucrose phosphorylase, polygalacturonase, polyfructan sucrase, ADP glucose pyrophosphorylase, cyclodextrin glycosyltransferase, fructosyl transferase, glycogen synthase, pectin esterase, aprotinin, avidin, bacterial levansucrase, *E. coli* glgA protein, MAPK4 and orthologues, nitrogen assimilation/methabolism enzyme, glutamine synthase, plant osmotin, 2S albumin, thaumatin, site-specific recombinase/integrase (FLP, Cre, R recombinase, Int, SSVI Integrase R, Integrase phiC31, or an active fragment or variant thereof), isopentenyl transferase, Sca M5 (soybean calmodulin), coleopteran type toxin or an insecticidally active fragment, ubiquitin conjugating enzyme (E2) fusion proteins, enzymes that metabolise lipids, amino acids, sugars, nucleic acids and polysaccharides, superoxide dismutase, inactive proenzyme form of a protease, plant protein toxins, traits altering fiber in fiber producing plants, Coleopteran active toxin from *Bacillus thuringiensis* (Bt2 toxin, insecticidal crystal protein (ICP), CrylC toxin, delta endotoxin, polyopeptide toxin, protoxin etc.), insect specific toxin AaIT, cellulose degrading enzymes, E1 cellulase from *Acidothermus celluloticus*, lignin modifying enzymes, cinnamoyl alcohol dehydrogenase, trehalose-6-phosphate synthase, enzymes of cytokinin metabolic pathway, HMG-CoA reductase, *E. coli* inorganic pyrophosphatase, seed storage protein, *Erwinia herbicola* lycopen synthase, ACC oxidase, pTOM36 encoded protein, phytase, ketohydrolase, acetoacetyl CoA reductase, PHB (polyhydroxybutanoate) synthase, acyl carrier protein, napin, EA9, non-higher plant phytoene synthase, pTOM5 encoded protein, ETR (ethylene receptor), plastidic pyruvate phosphate dikinase, nematode-inducible transmembrane pore protein, trait enhancing photosynthetic or plastid function of the plant cell, stilbene synthase, an enzyme capable of hydroxylating phenols, catechol dioxygenase, catechol 2,3-dioxygenase, chloromuconate cycloisomerase, anthranilate synthase, *Brassica* AGL15 protein, fructose 1,6-biphosphatase (FBPase), AMV RNA3, PVY replicase, PLRV replicase, potyvirus coat protein, CMV coat protein, TMV coat protein, luteovirus replicase, MDMV messenger RNA, mutant geminiviral replicase, *Umbellularia californica* C12:0 preferring acyl-ACP thioesterase, plant C10 or C12:0 preferring acyl-ACP thioesterase, C14:0 preferring acyl-ACP thioesterase (luxD), plant synthase factor A, plant synthase factor B, D6-desaturase, protein having an enzymatic activity in the peroxysomal b-oxidation of fatty acids in plant cells, acyl-CoA oxidase, 3-ketoacyl-CoA thiolase, lipase, maize acetyl-CoA-carboxylase, 5-enolpyruvylshikimate-3-phosphate synthase (EPSP), phosphinothricin acetyl transferase (BAR, PAT), CP4 protein, ACC deaminase, protein having posttranslational cleavage site, DHPS gene conferring sulfonamide resistance, bacterial nitrilase, 2,4D monooxygenase, acetolactate synthase or acetohydroxyacid synthase (ALS, AHAS), polygalacturonase, Taq polymerase, bacterial nitrilase, many other enzymes of bacterial or phage including restriction endonucleases, methylases, DNA and RNA ligases, DNA and RNA polymerases, reverse trascryptases, nucleases (Dnases and RNAses), phosphatases, transferases etc.

Our invention also can be used for the purpose of molecular farming and purification of commercially valuable and pharmaceutically important proteins including industrial enzymes (cellulases, lipases, proteases, phytases etc.) and fibrous proteins (collagen, spider silk protein, etc.). Any human or animal health protein can be expressed and purified using described in our invention approach. Examples of such proteins of interest include inter alia immune response proteins (monoclonal antibodies, single chain antibodies, T cell receptors etc.), antigens including those derived from pathogenic microorganisms, colony stimulating factors, relaxins, polypeptide hormones including somatotropin (HGH) and proinsulin, cytokines and their receptors, interferons, growth factors and coagulation factors, enzymatically active lysosomal enzyme, fibrinolytic polypeptides, blood clotting factors, trypsinogen, a1-antitrypsin (AAT), human serum albumin, glucocerebrosidases, native cholera toxin B as well as function-conservative proteins like fusions, mutant versions and synthetic derivatives of the above proteins.

Example 1

Use of Site-Specific DNA Recombination Trigerred by Protein-Switch to Assemble Amplifying Vector from Provector Parts Stably Integrated into the Plant Genome Binary vector pICHFPinv (FIG. 7) carrying T-DNA with two provector parts was designed using standard molecular biology techniques (Maniatis et al., 1982, Molecular cloning: a Laboratory Manual. Cold Spring Harbor Laboratory, New York). The descriptions of provector elements and basic principles of their construction and functionin are described in details in patent application PCT/EP02/03476 (WO02088369) and in DE 101 21 283. The vector carries transformation marker (NPTII gene), the 5'end of TMV preceded by the plant promoter of the *arabidopsis* actin 2 gene (An et al., 1996, Plant J., 10, 107-121) and contains an RNA dependent RNA polymerase (RdRp) and movement protein (MP) followed by a subgenomic promoter. The vector also contains 3' end of provector containing a gene of interest (GFP), viral coat protein (CP) providing for the systemic movement and 3'-nontranslated region of viral vector (3'NTR). The 3' provector together with two transcription termination signals is flanked by recombination sites recognised by phage integrase phiC31 (Thomason, Calendar & Ow, 2001, *Mol. Genet. Genomics*, 265, 1031-1038).

Transgenic *Nicotiana benthamiana* plants containing T-DNA of pICHGFPinv were obtained by *Agrobacterium*-mediated transformation of leaf discs as described by Horsch et al., (1985, Science, 227, 129-131). Leaf discs were incubated for 30 min with *Agrobacterium* strain GV3101 transformed with the construct of interest. After three days of incubation on medium (MS-medium 0.1 mgA NM, 1 mg/l BAP) without selective agent, selection of transformants was performed on the same MS-medium supplemented with 100 mg/L Kanamycin. In ordero reduce the growth of *Agrobacterium*, the medium was also supplemented with 300 mg/L carbenicilin and 300 mg/L cefataxime. Regenerants were incubated on selective MS-medium without hormones supplemented with the same concentration of the selective agents to induce the rooting. The presence of the transgene in segregating T2-populations was confirmed by PCR-analysis.

In order to produce a cell-permeable integrase or recombinase fused to the membrane translocation signal (MTS) of choice, the set of constructs for provector system (WO02088369) was made (see FIG. 9) according to standard molecular biology techniques. The integrase phiC31 was produced in *N. benthamiana* leaves, said integrase was fused to MTS of HIV-Tat48-60 (Wender et al., 2000, *Proc. Natl. Acad. Sci. USA*, 97, 13003-13008) or Kaposi Fibroblast Growth Factor (FGF) MTS (Lin et al., 1995, *J. Biol. Chem.*, 270, 14255-14258). The crude protein extract from infected *N. benthamiana* leaves was used for treatment of transgenic plants transformed with T-DNA of pICHGFPinv. In order to facilitate the penetration of the plant cell wall, an addition of cellulytic enzymes to crude protein extract containing the integrase, was used in some experiments. The 0.001% cellulase Onozuka R-10 (Serva) was used to increase the efficiency of the MTS-integrase fusion delivery into the plant cell.

Exposure of transgenic plant leaves to cell-permeable integrase causes site-specific recombination between attP and attB sites. Such recombination leads to the reversion of 3' provector, thus creating a complete cDNA of a viral amplicon under the control of the actin 2 promoter (FIG. 7, B). The TMV-based RNA amplicon expressing GFP is able for cell-to-cell and systemic movement The GFP expression in *N. benthamiana* plants can be easily detected using UV lamp or analyzing plant tissue under LEICA stereo fluorescent microscope system (excitation at 450-490 nm, emission at 500-550 nm). The sGFP used in our experiments can be excited by blue and UV-light.

The invention claimed is:

1. A method of controlling a genetically-modified plant, comprising:
   (a) providing a genetically-modified transgenic plant, whereby cells of said genetically-modified plant contain a heterologous nucleic acid and whereby said genetically-modified plant is inactive with regard to a cellular process of interest, and
   (b) switching on said cellular process of interest by directly introducing a polypeptide from a cell-free composition into cells of said transgenic plant containing said heterologous nucleic acid,
wherein said polypeptide and said heterologous nucleic acid are mutually adapted such that said polypeptide is capable of switching on said cellular process of interest; wherein said polypeptide comprises a covalently bound membrane translocation sequence enabling the direct introduction of said polypeptide into cells containing said heterologous nucleic acid;
   said polypeptide having an enzymatic activity of an enzyme selected from the group consisting of a site-specific recombinase and an integrase;
   wherein said cellular process of interest comprises formation of an expressible RNA amplicon from said heterologous nucleic acid by the enzymatic activity of said polypeptide;
   said RNA amplicon encoding an RNA-dependent RNA polymerase for amplifying said RNA amplicon and being capable of cell-to-cell or systemic movement in said plant.

2. The method of claim 1, wherein said directly introducing of step (b) is done by particle bombardment, application of said polypeptide on at least a part of said plant, or by injecting a solution containing said polypeptide in tissue of said plant.

3. The method of claim 1, wherein said switching on of said cellular process of interest further comprises formation of a protein from said heterologous nucleic acid or involving said heterologous nucleic acid, wherein cells of said genetically-modified plant contain an additional heterologous nucleic acid that is controlled by said protein.

4. The method of claim 3, wherein said protein is capable of spreading to other cells of said plant.

5. The method of claim 1, wherein said expressible amplicon is further capable of expressing a gene of interest.

6. The method of claim 4, wherein said protein further comprises a protein portion endowing said protein with the capability of leaving a cell and entering other cells of said plant.

7. The method of claim 6, wherein said protein portion is selected from the following group: a viral movement protein, viral coat protein, plant or animal transcription factor, plant or animal peptide intercellular messenger, and artificial peptide capable of endowing said protein with said capability.

8. The method of claim 6, wherein said protein is capable of controlling expression of said protein in cells containing said heterologous nucleic acid.

9. The method of claim 3, further comprising formation of an RNA or protein expression product, an operon, or an amplicon, from said additional heterologous nucleic acid.

10. The method of claim 3, wherein said protein and said polypeptide jointly generate a predetermined function switching on said cellular process of interest only when said protein and said polypeptide are jointly present.

11. The method of claim 10, wherein said protein and said polypeptide jointly generate said predetermined function by intein-mediated trans-splicing or by intein-mediated affinity interaction.

12. The method of claim 10, wherein said protein and said polypeptide jointly generate said predetermined function by affinity interaction mediated by leucine zipper fragments fused to said polypeptide and to said protein.

13. The method of claim 10, wherein said protein and said polypeptide jointly generate said predetermined function by affinity interaction mediated by dimerizer fragments fused to said polypeptide and to said protein.

14. The method of claim 13, wherein said affinity interaction is regulated by a dimerizer agent such as rapamycin or a rapamycin analog.

15. The method of claim 1, wherein said polypeptide is introduced in step (b) without introducing a nucleic acid coding for said polypeptide or for a part of said polypeptide capable of switching on said cellular process.

16. The method of claim 1, wherein said plant is a transgenic plant containing said heterologous nucleic acid stably integrated in the nuclear genome.

17. The method of claim 1, wherein said plant is a transgenic plant containing said heterologous nucleic acid stably integrated in the plastid genome.

18. The method of claim 1, wherein said plant is a higher crop plant.

19. A system of controlling a cellular process of interest in a genetically-modified plant, comprising
   (i) a genetically-modified transgenic plant containing a heterologous nucleic acid in cells thereof, wherein said plant is inactive with regard to a cellular process of interest, wherein said heterologous nucleic acid is adapted such that said cellular process of interest can be switched on by directly introducing a polypeptide into cells containing said heterologous nucleic acid, and
   (ii) a cell-free composition containing a polypeptide for switching on said cellular process of interest; said polypeptide having an enzymatic activity of an enzyme selected from the group consisting of a site-specific recombinase, and an integrase, wherein said polypeptide comprises a covalently bound membrane translocation sequence enabling the direct introduction of said polypeptide into cells containing said heterologous nucleic acid;
whereby said plant and said polypeptide are mutually adapted such that said polypeptide is capable of switching on said cellular process of interest;
   wherein said cellular process of interest comprises formation of an expressible RNA amplicon from said heterologous nucleic by the enzymatic activity of said polypeptide or by a binding affinity of said transcription factor to said heterologous nucleic acid or to an expression product of said heterologous nucleic acid;
   said RNA amplicon encoding an RNA-dependent RNA polymerase for amplifying said RNA amplicon and being capable of cell-to-cell or systemic movement in said plant.

* * * * *

SEQUENCE LISTING

<160> NUMBER OF SEQ ID NOS: 8

<210> SEQ ID NO 1
<211> LENGTH: 4
<212> TYPE: PRT
<213> ORGANISM: Homo sapiens

<400> SEQUENCE: 1

Asp Asp Asp Ile
1

<210> SEQ ID NO 2
<211> LENGTH: 11
<212> TYPE: PRT
<213> ORGANISM: Artificial Sequence
<220> FEATURE:
<223> OTHER INFORMATION: Membrane Translocation Signal

<400> SEQUENCE: 2

Arg Arg Arg Arg Arg Arg Arg Arg Arg Arg Arg
1               5                   10

<210> SEQ ID NO 3
<211> LENGTH: 27

-continued

```
<212> TYPE: PRT
<213> ORGANISM: Artificial Sequence
<220> FEATURE:
<223> OTHER INFORMATION: Membrane Translocation Signal

<400> SEQUENCE: 3

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 4
<211> LENGTH: 4
<212> TYPE: DNA
<213> ORGANISM: artificial sequence
<220> FEATURE:
<223> OTHER INFORMATION: membrane translocation sequence

<400> SEQUENCE: 4 rkkr                                                            4

<210> SEQ ID NO 5
<211> LENGTH: 16
<212> TYPE: PRT
<213> ORGANISM: Artificial Sequence
<220> FEATURE:
<223> OTHER INFORMATION: Membrane Translocation Signal

<400> SEQUENCE: 5

Arg Gln Ile Lys Ile Trp Phe Gln Asn Arg Arg Met Lys Trp Lys Lys
1               5                   10                  15

<210> SEQ ID NO 6
<211> LENGTH: 16
<212> TYPE: PRT
<213> ORGANISM: Artificial Sequence
<220> FEATURE:
<223> OTHER INFORMATION: Membrane Translocation Signal

<400> SEQUENCE: 6

Ala Ala Val Ala Leu Leu Pro Ala Val Leu Leu Ala Leu Leu Ala Pro
1               5                   10                  15

<210> SEQ ID NO 7
<211> LENGTH: 21
<212> TYPE: PRT
<213> ORGANISM: Artificial Sequence
<220> FEATURE:
<223> OTHER INFORMATION: Membrane Translocation Signal

<400> SEQUENCE: 7

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 8
<211> LENGTH: 13
<212> TYPE: PRT
<213> ORGANISM: Artificial Sequence
<220> FEATURE:
<223> OTHER INFORMATION: Membrane Translocation Signal

<400> SEQUENCE: 8

Gly Arg Lys Lys Arg Arg Gln Arg Arg Pro Pro Gln
1               5                   10
```